United States Patent [19]
Ingram et al.

[11] Patent Number: 6,102,690
[45] Date of Patent: Aug. 15, 2000

[54] RECOMBINANT ORGANISMS CAPABLE OF FERMENTING CELLOBIOSE

[75] Inventors: Lonnie O. Ingram; Xiaokuang Lai; Mohammed Moniruzzaman; Sean W. York, all of Gainesville, Fla.

[73] Assignee: Univ. of Florida Research Foundation, Inc., Gainsville, Fla.

[21] Appl. No.: 08/834,901

[22] Filed: Apr. 7, 1997

[51] Int. Cl.[7] .............................. C12P 7/06; C12N 15/00; C12N 1/20
[52] U.S. Cl. .................. 431/161; 435/252.3; 435/254.2; 435/195; 435/190; 435/189; 435/194; 435/320.1; 435/170; 536/23.2
[58] Field of Search .............................. 435/252.3, 254.2, 435/195, 190, 189, 194, 320.1, 161, 170, 69.1; 536/23.2

[56] References Cited

U.S. PATENT DOCUMENTS

| | | | |
|---|---|---|---|
| 4,464,471 | 8/1984 | Armentrout et al. | 435/253 |
| 5,000,000 | 3/1991 | Ingram et al. | 435/161 |
| 5,028,539 | 7/1991 | Ingram et al. | 435/161 |
| 5,424,202 | 6/1995 | Ingram et al. | 435/161 |
| 5,482,846 | 1/1996 | Ingram et al. | 435/161 |
| 5,487,989 | 1/1996 | Fowler et al | 435/165 |
| 5,514,583 | 5/1996 | Picataggio et al. | 435/252.3 |
| 5,554,520 | 9/1996 | Fowler et al. | 435/165 |
| 5,602,030 | 2/1997 | Ingram et al. | 435/252.3 |

OTHER PUBLICATIONS

Moniruzzaman, Mohammed et al., "Isolation and Molecular Characterization of High–Performance Cellobiose–Fermenting Spontaneous Mutants of Ethanologenic *Escherichia coli* KO11 Containing the *Klebsiella oxytoca casAB* Operon," *Applied and Environmental Microbiology* 63(12): 4633–4637 (1997).

Lai, X., et al., "Cloning of cellobiose phosphoenolpyruvate–dependent phosphotransferase genes: Functional expression in recombinant *Escherichia coli* and identification of a putative binding region for disaccharides", *Appl. Environ. Microbiol.*, 63:355–363, (1997).

Wood, B.E. and Ingram, L.O., "Ethanol production from cellobiose amorphous cellulose, and crystalline cellulose by recombinant *Klebsiella oxytoca* containing chromosomally integrated *Zymomonas mobilis* genes for ethanol production and plasmids expressing thermostable cellulase genes from *Clostridium thermocellum*", *Appl. Environ. Microbiol.*, 58:2103–2110, (1992).

Arfman, N., et al., "Use of the tac promoter and lacI$^q$ for the controlled expression of *Zymomonas mobilis* fermentative genes in *Escherichia coli* and *Zymomonas mobilis*", J. Bacteriol., 174:7370–7378, (1992).

Fox, C.F. and Wilson, G., "The role of a phosphoenolpyruvate–dependent kinase system in β–glucoside catabolism in *Escherichia coli*", *Proc. Natl. Acad. Sci. USA*, 59:988–995, (1968).

Lai, X. and Ingram, L.O., "Cloning and sequencing of a cellobiose phosphotransferase system operon from *Bacillus stearothermophilus* XL–65–6 and functional expression in *Escherichia coli*", *J. Bacteriol.*, 175:6441–6450, (1993).

(List continued on next page.)

*Primary Examiner*—Ponnathapu Achutamurthy
*Assistant Examiner*—Bradley S. Mayhew
*Attorney, Agent, or Firm*—Lahive & Cockfield, LLP; Elizabeth A. Hanley; Peter C. Lauro

[57] ABSTRACT

This invention relates to a recombinant microorganism which expresses pyruvate decarboxylase, alcohol dehydrogenase, Klebsiella phospho-β-glucosidase and Klebsiella (phosphoenolpyruvate-dependent phosphotransferase system) cellobiose-utilizing Enzyme II, wherein said phospho-β-glucosidase and said (phosphoenolpyruvate-dependent phosphotransferase) cellobiose-utilizing Enzyme II are heterologous to said microorganism and wherein said microorganism is capable of utilizing both hemicellulose and cellulose, including cellobiose, in the production of ethanol.

38 Claims, 10 Drawing Sheets

MODEL FOR CELLOBIOSE METABOLISM IN CERTAIN BACTERIA

OTHER PUBLICATIONS

Lai, X. and Ingram, L.O., "Discovery of a ptsHI operon, which includes a third gene (pstT), in the thermophile *Bacillus stearothermophilus*", *Microbiology*, 141:1443–1449, (1995).

Misawa, N. and Nakamura, K., "Expression and stability of a β–glucosidase gene of *Ruminococcus albus* in *Zymomonas mobilis*", *Agric. Biol. Chem.*, 53:723–727, (1989).

Rogers, P.L., et al., "Ethanol production by *Zymomonas mobilis*", *Adv. Biochem. Eng.*, 23:37–84, (1982).

Saffen, D.W., et al., "Sugar transport by the bacterial phosphotransferase system. Molecular cloning and structural analysis of the *Escherichia coli ptsH, pts1*, and crr genes", *J. Biol. Chem.*, 262:16241–16253, (1987).

Sprenger, G.A., "Approaches to broaden the substrate and product range of the ethanologenic bacterium *Zymomonas mobilis* by genetic engineering", *J. Biotech.*, 27:225–237, (1993).

Su, P., et al., "Cloning and expression of a β–glucosidase gene from *Xanthomonas albilineans* in *Escherichia coli* and *Zymomonas mobilis*", *J. Biotech.*, 9:139–152, (1989).

Yomano, L.P., et al., "Cloning, sequencing, and expression of the *Zymomonas mobilis* phosphoglycerate mutase gene (pgm) in *Escherichia coli*", *J. Bacteriol.*, 175:3926–3933, (1993).

```
                              M  T  M  I  T  N  S  S  S  V  P  G-->
pUC18  TCGTATGTTGTGTGGAATTGTGAGCGGATAACAATTTCACACAGGAAACAGCTATGACCATGATTACGAATTCGAGCTCGGTACCCGGG (BamHI)
       ----- ----            ----- ---               * * **  *                  * ** *
1916   CTCGGGTTTTTTATTTTAATACTCAGTTAACGATGCCTGCGGGCAGCGGAAGTAAGGAAAAACAGCATGGAATATAAAGCACTCGCG
                                                                    M  E  Y  K  A  L  A-->
1908   TCGTATGTTGTGTGGAATTGTGAGCGGATAACAATTTCACACAGGAAACAGC//AAGGAAAAACAGCATGGAATATAAAGCACTCGCG
                                                                    M  E  Y  K  A  L  A-->
1910   TCGTATGTTGTGTGGAATTGTGAGCGGATAACAATTTCACACAGGAAACAG//TAAGGAAAAACAGCATGGAATATAAAGCACTCGCG
                                                                    M  E  Y  K  A  L  A-->
```

FIG. 3B

RECOMBINANT ORGANISMS CAPABLE OF FERMENTING CELLOBIOSE

GOVERNMENT FUNDING PARAGRAPH

The invention described herein was made with government support provided, through the Florida Agricultural Experiment Station (Grant No. FLA-MCS-03445), Department of Energy, Office of Basic Energy Sciences (Grant No. DE-FG02-96ER20222) and U.S. Department of Agriculture, National Research Initiative (Grant No. 95-37308-1843). The government has certain rights in the invention.

BACKGROUND OF THE INVENTION

Most fuel ethanol is currently produced from hexose sugars in corn starch or cane syrup utilizing *S. cerevisiae* or *Z. mobilis*. However, such sugars are a relatively expensive source of biomass sugars and have competing value as foods. Alternatively, a major and cheap, renewable source of biomass is present in waste paper and yard trash from landfills, in the form of lignocellulose. Lignocellulose is primarily a mixture of cellulose, hemicellulose, and lignin. Cellulose is a homopolymer of glucose, while hemicellulose is a more complex heteropolymer comprised not only of xylose, which is its primary constituent, but also of significant amounts of arabinose, mannose, glucose and galactose. It has been estimated that microbial conversion of the sugar residues present in this abundant source of biomass (waste paper and yard trash) could provide over ten billion gallons of ethanol.

Recombinant microorganisms are known which can effectively ferment the mixture of sugars, formed by the hydrolysis of hemicellulose, into ethanol. See, for example, U.S. Pat. No. 5,028,539 to Ingram et al., U.S. Pat. No. 5,000,000 to Ingram et al., U.S. Pat. No. 5,424,202 to Ingram et al., U.S. Pat. No. 5,487,989 to Fowler et al., U.S. Pat. No. 5,482,846 to Ingram et al., U.S. Pat. No. 5,554,520 to Fowler et al., U.S. Pat. No. 5,514,583 to Picataggio, et al., and copending applications having U.S.S.N 08/363,868 filed on Dec. 27, 1994, U.S.S.N. 08/475,925 filed on Jun. 7, 1995, U.S.S.N. 08/218,914 filed on Mar. 28, 1994the teachings of all of which are hereby incorporated by reference, in their entirety. Likewise, these patents and applications describe recombinant microorganisms that can ferment the product of both the complete and partial hydrolysis of cellulose, namely glucose and the disaccharide, cellobiose into ethanol.

However, it would be highly advantageous to develop a single organism which could utilize both hemicellulose hydrolysates and cellulose hydrolysates, particularly the disaccharide, cellobiose, in the process of producing ethanol through fermentation in high yields.

SUMMARY OF THE INVENTION

The invention is based upon the discovery that the insertion of a *Klebsiella oxytoca* cas AB operon into an ethanologenic microorganism, such as *Escherichia coli* KO11 or *Zymomonas mobilis* CP4, provides an improved cellobiose transport system, thereby providing a recombinant microorganism with an improved ability to ferment cellulosic materials to ethanol. The *K. oxytoca* cas AB operon encodes a (phosphoenolpyruvate-dependent phosphotransferase system) cellobiose-utilizing Enzyme II and phospho-β-glucosidase.

Thus, in one embodiment, the invention described herein relates to novel recombinant ethanologenic microorganisms which can effectively transport cellobiose, thereby permitting the microorganism to utilize both hemicellulose and cellulose in the production of ethanol. The microorganisms can be characterized by a heterologous isolated nucleic acid molecule *K. oxytoca* cas AB operon which encodes a (phosphoenolpyruvate-dependent phosphotransferase system) cellobiose-utilizing Enzyme II and phospho-β-glucosidase. The cellobiose-utilizing Enzyme II is obtained from the phosphoenolpyruvate-dependent phosphotransferase system. The microorganisms are preferably organisms which are capable of fermenting xylose, glucose or both to ethanol. The invention further relates to isolated and/or recombinant nucleic acid molecules which encode the *K. oxytoca* cas AB operon, including homologs, active fragments or mutants thereof, the proteins encoded by these isolated and/or recombinant nucleic acid molecules, the plasmids containing the *K. oxytoca* cas AB operon, and the methods of using these novel recombinant organisms in the production of ethanol.

In one aspect, the present invention relates to recombinant microorganisms which express pyruvate decarboxylase (also referred to as pdc), alcohol dehydrogenase (also referred to as adh), Klebsiella phospho-β-glucosidase and Klebsiella (phosphoenolpyruvate-dependent phosphotransferase system) cellobiose-utilizing Enzyme II. In general, the recombinant microorganisms express the above, at a sufficient functional level so as to facilitate the production of ethanol as a primary fermentation product, in high yields.

The Klebsiella phospho-β-glucosidase and Klebsiella (phosphoenolpyruvate-dependent phosphotransferase system) cellobiose-utilizing Enzyme II, are heterologous to (i.e. foreign to) the recombinant microorganism, whereas, the pyruvate decarboxylase and alcohol dehydrogenase can be either native to or heterologous to the recombinant microorganism.

In specific embodiments, the pyruvate decarboxylase and/or alcohol dehydrogenase, of the recombinant microorganisms, are encoded by nucleic acid molecules of Zymomonas origin. In more specific embodiments, the pyruvate decarboxylase and/or alcohol dehydrogenase, of the recombinant microorganisms, have the same or substantially the same amino acid sequence as the corresponding enzyme as it would be expressed by *Zymomonas mobilis* (hereinafter *Z. mobilis*).

In certain embodiments, the Klebsiella phospho-β-glucosidase and/or the Klebsiella(phosphoenolpyruvate-dependent phosphotransferase system) cellobiose-utilizing Enzyme II, are encoded by a nucleic acid molecule of *Klebsiella oxytoca* origin. In other embodiments, the phospho-β-glucosidase has the same or substantially the same amino acid sequence as *Klebsiella oxytoca* phospho-β-glucosidase. In further embodiments, the (phosphoenolpyruvate-dependent phosphotransferase system) cellobiose-utilizing Enzyme II, has the same or substantially the same amino acid sequence as Klebsiella oxytoca (phosphoenolpyruvate-dependent phosphotransferase system) cellobiose-utilizing Enzyme II.

A second aspect of the invention relates to a recombinant microorganism comprising heterologous nucleic acid molecules encoding a Zymomonas pyruvate decarboxylase, a Zymomonas alcohol dehydrogenase, a Klebsiella phospho-β-glucosidase and a Klebsiella (phosphoenolpyruvate-dependent phosphotransferase system) cellobiose-utilizing Enzyme II, wherein said molecules are expressed at levels sufficient to convert cellobiose to ethanol. In certain embodiments, the microorganism has been further mutated, for example, spontaneously or from contact with a mutagen. In an additional embodiment, the mutated microorganism has been subjected to an enrichment selection, for example, in cellobiose-medium, according to methods generally known in the art and described herein and in copending application U.S.S.N. 08/363,868 filed Dec. 27, 1994 and Attorney Docket No. UF97-02 filed Apr. 7, 1997 which are incorporated herein by reference.

In one preferred embodiment of this aspect of the invention, the Zymomonas is *Zymomonas mobilis*. In another preferred embodiment, the Klebsiella is *Klebsiella oxytoca*.

In a specific embodiment, the recombinant microorganism comprises heterologous nucleic acid molecules encoding *Zymomonas mobilis* pyruvate decarboxylase and alcohol dehydrogenase and *Klebsiella oxytoca* phospho-β-glucosidase and (phosphoenolpyruvate-dependent phosphotransferase system) cellobiose-utilizing Enzyme II. In further specific embodiments, the heterologous nucleic acid molecules are inserted into the microorganism as a single plasmid. In particular embodiments, the heterologous nucleic acid molecules which are inserted into the microorganism as a single plasmid are under a common regulatory control which can be either endogenous to or heterologous to the microorganism. In particular embodiments, the heterologous nucleic acid molecules which are inserted into the microorganism as the single plasmid are located on a plasmid in the microorganism. In an alternative embodiment, the heterologous nucleic acid molecules which are inserted into the microorganism as the single plasmid are chromosomally integrated in the microorganism.

In yet another particular embodiment, the heterologous nucleic acid molecules encoding *Zymomonas mobilis* pyruvate decarboxylase and alcohol dehydrogenase are inserted into the recombinant microorganism in a separate plasmid from the heterologous nucleic acid molecules encoding *Klebsiella oxytoca* phospho-β-glucosidase and (phosphoenolpyruvate-dependent phosphotransferase system) cellobiose-utilizing Enzyme II. In a specific embodiment, at least one of the heterologous nucleic acid molecules inserted in the separate plasmids is under regulatory control which is endogenous to the microorganism. In another specific embodiment, at least one of the heterologous nucleic acid molecules inserted in the separate plasmids is under regulatory control which is heterologous to the microorganism. In further embodiments, at least one of the heterologous nucleic acid molecules inserted in the separate plasmids is located on a plasmid in the microorganism, and alternatively at least one of the heterologous nucleic acid molecules inserted in the separate plasmids is chromosomally integrated in the microorganism.

The availability of a single organism capable of efficiently converting glucose and xylose to ethanol, and transporting cellobiose into the organism for metabolism would allow improved co-fermentation, thereby eliminating the need for separation of solids and washing after hydrolysis, as would be necessary in procedures where separate fermentation is required. The elimination of these steps would lead to a significant reduction in cost. In addition, since both substrates (hemicellulose and cellulose) can be used to make ethanol, monomer sugar concentrations and cellulose concentrations can each be lower than required for separate fermentation and still achieve equivalent final ethanol concentration. This also would be a significant cost savings and could allow for a shift from high solids reactors, which are very energy intensive and complex, to plugged flow reactors with pumping of solids as a slurry.

BRIEF DESCRIPTION OF THE DRAWINGS

FIG. 3B shows an alignment of nucleotide sequences depicting the regions of plasmids pLOI1908, pLOI1909 and pLOI1910, which contain deletions of portions of vector DNA and of *K. oxytoca* DNA in comparison with the original plasmid pLOI1906.

DETAILED DESCRIPTION OF THE INVENTION

Figure 1:
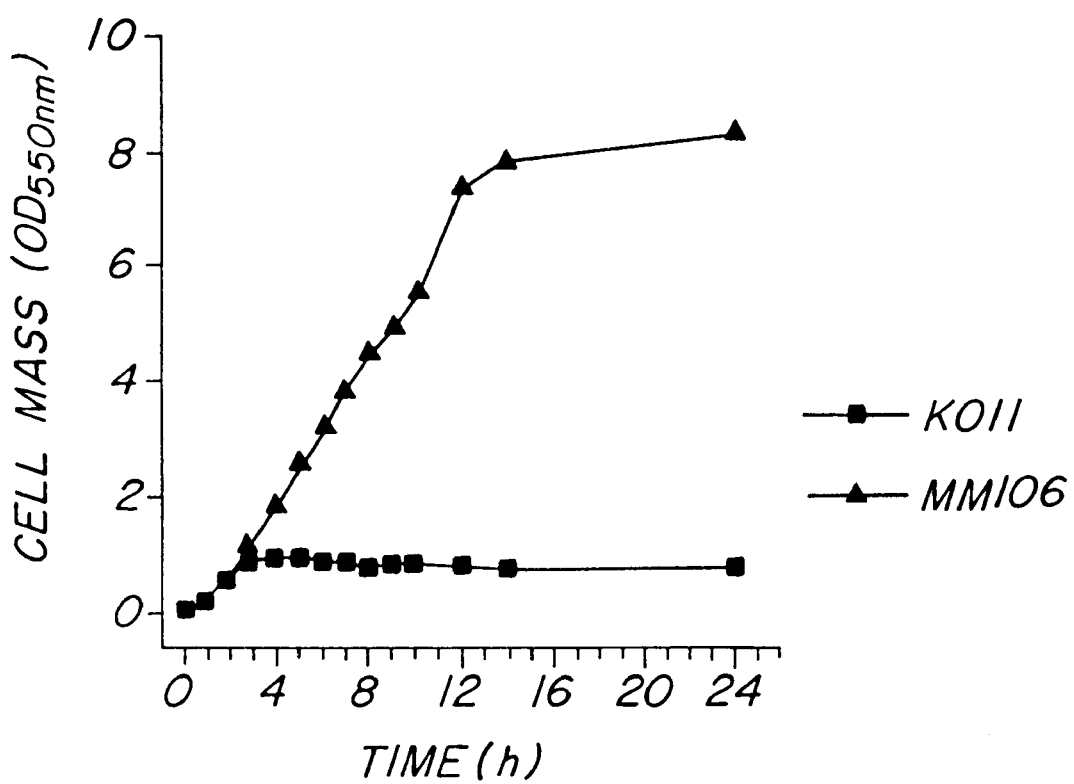
FIG. 1 is a comparison of growth (shaken flasks) in Luria broth containing cellobiose (50 g liter$^{-1}$) of the parental strain (KO11 harboring plasmid pLOI1906)and mutant strain MM106. Cultures were incubated at 35° C. in shaken flask (250 ml) containing 50 ml of Luria broth with cellobiose (60 g liter$^{-1}$).

*Escherichia coli* B has been previously engineered for ethanol production from soluble sugars by, for example, the chromosomal integration of *Zymomonas mobilis* genes encoding pyruvate decarboxylase (also referred to as pdc) and alcohol dehydrogenase (also referred to as adhB), to produce *E. coli* KO11. This particular strain, *E. coli* KO11, is included in Table 1, along with other recombinant microorganisms previously engineered for use in the conversion of, for example, lignocellulose to ethanol.

Another recombinant microorganism included in the Table, *K. oxytoca* M5A1 P2, is of particular interest. As indicated in the Table, *K. oxytoca* M5A1 P2 is a derivative of *K. oxytoca* in which the *Zymomonas mobilis* pdc and adhB genes have been chromosomally integrated. It has been found that *K. oxytoca* M5A1 P2 can rapidly and efficiently convert cellobiose to high levels of ethanol. Cellobiose is a disaccharide obtained upon partial hydrolysis of cellulose and acts as an inhibitor of endoglucanase and exoglucanase. It is known that hydrolysis of cellobiose to monomeric sugar by β-glucosidase often limits cellulose digestion by fungal broths, due to inhibition of β-glucosidase by cellobiose. *K. oxytoca* M5A1 P2 appears to have the capacity to actively transport and metabolize cellobiose, eliminating the need for β-glucosidase and reducing end-product inhibition of cellulases by cellobiose.

TABLE 1

| Bacteria (Plasmid) | Characteristics | Accession Number (Deposit Date) |
|---|---|---|
| K. oxytoca M5A1 (pLOI555) | Cm$^r$, pet$^b$ | ATCC 68564 |
| K. oxytoca M5A1 S1 | Cm$^r$, Ipet$^a$ | |
| K. oxytoca M5A1 S2 | Cm$^r$, Ipet$^a$ | |
| K. oxytoca M5A1 S3 | Cm$^r$, Ipet$^a$ | |
| K. oxytoca M5A1 P1 | Cm$^r$, Ipet$^a$ | |
| K. oxytoca M5A1 P2 | Cm$^r$, Ipet$^a$ | |
| K. oxytoca M5A1 B1 | Cm$^r$, Ipet$^a$ | |
| E. coli KO11 | frd, Cm$^r$, pet$^a$ | |
| E. coli (pLOI510) | pet$^c$ | ATCC 68484 (11/28/90) |
| E. coli (pLOI308-10) | pet$^c$ | ATCC 67983 (5/15/89) |
| E. coli C4 (pLOI292) | pet$^c$ | ATCC 68237 (2/23/90) |
| E. coli TC4 (pLOI308-11) | pet$^c$ | ATCC 68238 (2/23/90) |
| E. coli TC4 (pLOI297) | pet$^c$ | ATCC 68239 (2/23/90) |
| E. coli TC4 (pLOI295) | pet$^c$ | ATCC 68240 (2/23/90) |

$^a$Ipet refers to the integration of Z. mobilis pdc and adhB genes into the chromosome.
$^b$pet refers to the presence of Z. mobilis pdc and adhB genes in plasmid pLOI555.
$^c$pet refers to the presence of Z. mobilis pdc and adhB genes in the indicated plasmid.
Cm$^r$ is the an E. coli shuttle vector carrying the cat gene.

A more detailed description of these and other related recombinant organisms, as well as the techniques and materials used in their preparation can be found in, for example, U.S. Pat. No. 5,028,539 to Ingram et al., U.S. Pat. No. 5,000,000 to Ingram et al. U.S. Pat. No. 5,424,202 to Ingram et al., U.S. Pat. No. 5,487,989 to Fowler et al., U.S. Pat. No. 5,482,846 to Ingram et al., U.S. Pat. No. 5,554,520 to Fowler et al., U.S. Pat. No. 5,514,583 to Picataggio, et al., U.S. Pat. No. 5,821,043 to Ingram et al, copending applications, U.S.S.N. 08/475,925 filed on Jun. 7, 1995, U.S.S.N. 08/218, 914 filed on Mar. 28, 1994, U.S.S.N. 08/834,900, filed on Apr. 7, 1997 and U.S.S.N. 08/833,435, filed on Apr. 7, 1997 and standard texts such as, Ausubel et al., *Current Protocols in Molecular Biology*, Wiley-Interscience, New York (1988) (hereinafter "Ausubel et al."), Sambrook et al., *Molecular Cloning: A Laboratory Manual*, Third Edition, Cold Spring Harbor Laboratory Press (1992) (hereinafter "Sambrook et al.") and *Bergey's Manual of Systematic Bacteriology*, William & Wilkins Co., Baltimore (1984) (hereinafter "Bergey's Manual") the teachings of all of which are hereby incorporated by reference in their entirety.

The *E. coli* KO11 recombinant microorganism described above, has been shown to efficiently convert to ethanol the mixture of sugars which result from the hydrolysis of hemicellulose, while the *K. oxytoca* M5A1 P2 has been shown to rapidly and efficiently convert cellulose and cellobiose to high levels of ethanol.

The invention is based upon the discovery that the insertion of the *Klebsiella oxytoca* cas AB operon into an ethanologenic microorganism, such as *Escherichia coli* KO11 or *Zymomonas mobilis* CP4, provides an improved cellobiose transport system, thereby providing a recombinant microorganism with an improved ability to ferment cellulosic materials to ethanol.

The K. oxytocacas AB operon of the invention encodes a (phosphoenolpyruvate-dependent phosphotransferase system) cellobiose-utilizing Enzyme II and phospho-β-glucosidase. Appropriate regulatory sequences can be operably linked to the coding sequence and include, for example, enhancers, promoters (native or heterologous), inducers, operators, ribosomal binding sites and transcriptional terminators. Other species of Klebsiella suitable for isolating the nucleic acids for use in this invention include, for example, *Klebsiella pneumoniae*, *Klebsiella terrigena* and *Klebsiella planticola*.

The cellobiose-utilizing Enzyme II, as described herein, comprises an integral membrane protein which forms the transmembrane channel and catalyzes the phosphorylation of cellobiose, as part of the phosphotransferase system (also referred to as PTS), native to *Klebsiella oxytoca*. This system can also include a protein termed Enzyme III and/or a protein termed Enzyme I and/or a protein termed HPr (See Stryer, *Biochemistry*, Third Edition, W. H. Freeman and Co., New York (1988) p 959–961, the teachings of which are incorporated herein by reference). The phosphotransferase system is a phosphoenolpyruvate-dependent system, since the phosphoryl donor is phosphoenolpyruvate, rather than, for example, ATP or another nucleoside triphosphate. The overall effect of the PTS in *Klebsiella oxytoca* is transport of cellobiose inside the bacterium where it is present in the phosphorylated form. As such, nucleic acids encoding other proteins implicated in cellobiose transport can additionally be cloned into the host cell. For example, the nucleic acid molecule can encode active Enzyme I, Enzyme III or HPr of the PTS. Genes encoding PTS systems for cellobiose metabolism have been cloned from 7 different bacteria by screening libraries with methylumbelliferyl-$\beta$-D-glucopyranoside, a chromogenic analogue of cellobiose, and are described in detail, including the techniques used, in Lai, et al., *Appl. Environ. Microbiol.* 63: 355–363 (1997), the entire teachings of which are hereby incorporated by reference in its entirety. Phospho-$\beta$-glucosidase, as described herein, is an enzyme responsible for converting phosphorylated cellobiose into the corresponding glucose monomers.

Thus, the invention described herein relates to novel recombinant ethanologenic microorganisms which can effectively transport cellobiose, thereby permitting the microorganism to utilize both hemicellulose and cellulose in the production of ethanol. Cellulose, as defined herein, is a homopolymer of glucose; hemicellulose is a more complex heteropolymer comprised not only of xylose, which is its primary constituent, but also of significant amounts of arabinose, mannose, glucose and galactose; and cellobiose is a disaccharide obtained upon the partial hydrolysis of cellulose.

The microorganisms can be characterized by a heterologous isolated nucleic acid molecule *K. oxytoca* cas AB operon which encodes a (phosphoenolpyruvate-dependent phosphotransferase system) cellobiose-utilizing Enzyme II and phospho-$\beta$-glucosidase, described in detail above. The microorganisms are preferably organisms which are capable of fermenting both xylose, glucose or both to ethanol.

The invention further relates to isolated and/or recombinant nucleic acid molecules which encode the *K. oxytoca* cas AB operon, described above. The isolated nucleic acid molecule can be, for example, a nucleotide sequence, such as a deoxyribonucleic (DNA) sequence or a ribonucleic acid (RNA) sequence. The isolated nucleic acid molecule can also comprise a nucleotide sequence which results from a silent mutation. Such a nucleotide sequence can result, for example, from a mutation of the native sequence in which one or more codons have been replaced with a degenerate codon, that is, a codon which encodes the same amino acid. Such mutant nucleotide sequences can be constructed using methods which are well known in the art, for example the methods discussed by Ausubel et al. and Sambrook et al.

The isolated nucleic acid molecules can also comprise a nucleotide sequence which encodes active fragments of the *K. oxytoca* cas AB operon proteins.

The isolated nucleic acid molecules also comprise a nucleotide sequence which is homologous to the nucleotide sequence which encodes the *K. oxytoca* cas AB operon. Such a nucleotide sequence exhibits more than 80% homology with the nucleotide sequence of the *K. oxytoca* cas AB operon, preferably more than about 90% homology. Particularly preferred sequences have at least about 95% homology or have substantially the same sequence. Preparation of mutant nucleotide sequences can be accomplished by methods known in the art as described in old, et al., *Principles of Gene Manipulation*, Fourth Edition, Blackwell Scientific Publications (1989), in Sambrook et al., and in Ausubel et al.

The invention also relates to the active protein(s) encoded by the nucleic acid molecules described above. The proteins of the invention can also be recombinant proteins produced by heterologous expression of the nucleic acid molecules which encode the *K. oxytoca* cas AB operon protein(s) or a silent mutation thereof, as discussed above. The active proteins of the invention can have an amino acid sequences which are homologous to the amino acid sequences expressed by the *K. oxytoca* cas AB operon. The term "homologous", as used herein, describes a protein having at least about 80% sequence identity or homology with the reference protein, and preferably about 90i sequence homology, in an amino acid alignment. Most preferably, the protein exhibits at least about 950 homology or substantially the same sequence as the disclosed sequence. A homologous protein can also have one or more additional amino acids appended at the carboxyl terminus or amino terminus, such as a fusion protein.

The homologous proteins of the invention can also be non-naturally occurring. In general, a homologous protein can be a mutant protein which has a modified amino acid sequence resulting from the deletion, insertion or substitution of one or more amino acid residues in the amino acid sequence to which it is referenced, for example, in this invention expressed by the *K. oxytoca* cas AB operon. Both conservative and non-conservative substitutions (including deletions and insertions) can be made in the amino acid sequence. Conservative substitutions are those in which a first amino acid residue is substituted by a second residue having similar side chain properties. An example of such a conservative substitution is replacement of one hydrophobic residue, such as valine, with another hydrophobic residue, such as leucine. A non-conservative substitution involves replacing a first residue with a second residue having different side chain properties. An example of this type of substitution is the replacement of a hydrophobic residue, such as valine, with an acidic residue, such as glutamic acid.

Generally, nucleotides and, therefore, amino acids which can be mutated can be identified by aligning the sequence to be mutated with homologous sequences of similar function from other organisms. It is typically desirable to retain highly conserved amino acids, particularly amino acids implicated in the binding or catalytic activities of the protein.

Such amino acid sequence variants can be prepared by methods known in the art. For example, the desired variants can be synthesized in vitro using known methods of peptide synthesis. The amino sequence variants are preferably made by introducing appropriate nucleotide changes into a DNA molecule encoding the native protein, followed by expression of the mutant enzyme in an appropriate vector. These methods include site-directed mutagenesis or random mutagenesis, for example.

In yet another embodiment, the nucleic acid molecule of the present invention can be a nucleic acid molecule, such as a recombinant DNA molecule, resulting from the insertion into its chain by chemical or biological means, of one or more of the nucleotide sequences described above. Recombinant DNA includes any DNA synthesized by procedures using restriction nucleases, nucleic acid hybridization, DNA cloning, DNA synthesis or any combination of the preceding. Methods of construction can be found in Sambrook et al. and Ausubel et al., and additional methods are known to those skilled in the art.

The invention also includes a plasmid or vector comprising a recombinant DNA sequence or molecule which comprises one or more of the nucleic acid molecules, e.g. nucleotide sequences, of the invention, as described above. The terms "plasmid" and "vector" are intended to encompass any replication competent plasmid or vector capable of having foreign or exogenous DNA inserted into it by chemical or biological means and subsequently, when transformed into an appropriate non-human host organism, of expressing the product of the foreign or exogenous DNA insert (e.g, of expressing the *K. oxytoca* cas AB operon of the present invention). In addition, the plasmid or vector is receptive to the insertion of a DNA molecule or fragment thereof containing the gene or genes of the present invention encoding the *K. oxytoca* cas AB operon as described herein. Procedures for the construction of DNA plasmid vectors include those described in Sambrook et al. and Ausubel et al. and others known to those skilled in the art.

In a certain embodiment, the recombinant microorganisms of the invention express pyruvate decarboxylase, alcohol dehydrogenase, Klebsiella phospho-β-glucosidase and Klebsiella (phosphoenolpyruvate-dependent phosphotransferase system) cellobiose-utilizing Enzyme II.

Alcohol dehydrogenase and pyruvate decarboxylase are enzymes required for alcoholic fermentation. The net reaction for alcoholic fermentation and the intermediate reactions for the regeneration of NAD⁺, in alcoholic fermentation are as follows: Intermediate:

Intermediate:
2 Pyruvate → 2 Acetaldehyde + 2 CO$_2$
2 Acetaldehyde + 2 NADH → 2 Ethanol + 2 NAD⁺
Net:
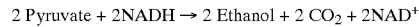
2 Pyruvate + 2NADH → 2 Ethanol + 2 CO$_2$ + 2NAD⁺

Pyruvate decarboxylase is the enzyme responsible for the cleavage of pyruvate into acetaldehyde and carbon dioxide, as shown in the above reaction. Alcohol dehydrogenase is the enzyme responsible for the regeneration of NAD⁺, by transferring hydrogen equivalents from NADH to acetaldehyde, thereby producing ethanol, as represented in the above reactions.

For purposes of this invention, the alcohol dehydrogenase activity can be provided from a gene isolated from, for example, a horse, yeast, human, insect or bacteria such as, Zymomonas, for example *Zymomonas mobilis*. Many alcohol dehydrogenase genes are well known to those skilled in the art, as evidenced by the recitation of 252 alcohol dehydrogenase genes in the Genbank database as of arch 1991 (IntelliGenetics Inc., 700 E. El Camino Drive, Mountain View, Calif., 94040). Likewise, the pyruvate decarboxylase activity can be provided by a gene from Zymomonas, such as *Zymomonas mobilis* or by a gene which encodes the needed enzymatic activity but which comes from corn, yeast or some other organism. At least 5 pyruvate decarboxylase genes are listed in GenBank database as of March, 1991. Therefore, one of skill in the art using standard techniques is able to isolate functionally equivalent, genetically related enzymes of pyruvate decarboxylase and alcohol dehydrogenase from a variety of sources using primary information from one or more members of an enzyme family. In the case of these particular enzymes, other genes can be located without sequence information, since both the pyruvate decarboxylase and alcohol dehydrogenase activity can be observed directly on aldehyde indicator plates using methods well known in the art.

The Klebsiella phospho-β-glucosidase and Kelbsiella (phosphoenolpyruvate-dependent phosphotransferase system) cellobiose-utilizing Enzyme II are heterologous to (i.e. foreign to) the recombinant microorganism, whereas, the pyruvate decarboxylase and alcohol dehydrogenase can be native to or heterologous to the recombinant ethanologenic microorganism. Therefore, the recombinant microorganisms can be organisms other than Klebsiella and are preferably organisms which are capable of fermenting both xylose, glucose or both to ethanol.

For example, organisms suitable for modification in this invention include, inter alia, eukaryotic cells, such as animal cells, insect cells, fungal cells, yeasts and bacteria, particularly bacteria and yeasts. Preferred host cells are bacteria and yeasts which, naturally or through mutation or recombinant engineering, encode enzymes required for the conversion of sugars (particularly glucose and/or xylose) to ethanol. As such, the host cells can be gram-negative or gram-positive bacteria or yeasts.

Recombinant bacteria which have been engineered to convert both glucose and xylose to ethanol are particularly preferred. For example, *E. coli* and other enteric bacteria of the genera Erwinia, like *E. chrysanthemi* are attractive because they can metabolize a variety of sugars. Other suitable hosts can be selected from the broader category of gram-negative bacteria, such as species of the genus Xanthomonas, and from the gram-positive bacteria, such as members of the genera Bacillus, for example, *B. pumilus, B. Subtilis* and *B. coagulans*, members of the genera Clostridium, for example, *Cl. acetobutylicum, Cl. aerotolerans, Cl. thermocellum, Cl. thermohydrosulfuricum* and *Cl. thermosaccharolyticum*, member of the genera Cellulomanas like *C. uda* and Butyrivibrio fibrisolvens. Acceptable yeasts, for example, are of the species of Cryptococcus like *Cr. albidus*, Monilia, *Pichia stipitis*, and *Pullularia pullulans*. Another preferred microorganism is *Zymomonas mobilis*.

In specific embodiments, the pyruvate decarboxylase and/or alcohol dehydrogenase of the recombinant microorganisms, are encoded by a nucleic acid molecule of Zymomonus origin, preferably *Z. mobilis* (See Bergey's Manual). Briefly, *Z. mobilis* is an obligatively fermentative bacterium which lacks a functional system for oxidative phosphorylation. Like the yeast *Saccharomyces cerevisiae, Z. mobilis* produces ethanol and carbon dioxide as principal fermentation products. *Z. mobilis* has long served as an inoculum for palm wines and for the fermentation of Agave sap to produce pulque, an alcohol-containing Mexican beverage. The microbe also is used in the production of fuel ethanol, and reportedly is capable of ethanol production rates which are substantially higher than that of yeasts. In a further embodiment, the pyruvate decarboxylase and/or alcohol dehydrogenase expressed by the recombinant microorganisms have the same or substantially the same amino acid sequence as the corresponding enzyme as it would be expressed by *Z. mobilis*.

In certain embodiments, the Klebsiella phospho-β-glucosidase and/or the Klebsiella(phosphoenolpyruvate-dependent phosphotransferase system) cellobiose-utilizing Enzyme II, are encoded by a nucleic acid molecule of

*Klebsiella oxytoca* origin (See Bergey's Manual). In other embodiments, the phospho-β-glucosidase has the same or substantially the same amino acid sequence as *Klebsiella oxytoca* phospho-β-glucosidase. In further embodiments, the (phosphoenolpyruvate-dependent phosphotransferase system) cellobiose-utilizing Enzyme II, has the same or substantially the same amino acid sequence as *Klebsiella oxytoca* (phosphoenolpyruvate-dependent phosphotransferase system) cellobiose-utilizing Enzyme II.

A second aspect of the invention relates to a recombinant microorganism comprising heterologous nucleic acid molecules encoding a Zymomonas pyruvate decarboxylase, a Zymomonas alcohol dehydrogenase, a Klebsiella phospho-β-glucosidase and a Klebsiella (phosphoenolpyruvate-dependent phosphotransferase system) cellobiose-utilizing Enzyme II, wherein said molecules are expressed at levels sufficient to convert cellobiose to ethanol. In certain embodiments, the microorganism has been further mutated, for example, spontaneously or from contact with a mutagen. Suitable mutagens include radiation, e.g., ultraviolet radiation, and chemical mutagens, such as N-methyl-N'nitrosoguanidines, hydroxylamine, ethylmethanesulfonate and nitrous acid. In an additional embodiment, the mutated microorganism has been subjected to an enrichment selection, for example, in cellobiose-medium, according to methods generally known in the art and described herein.

In one preferred embodiment of this aspect of the invention, the Zymomonas is *Zymomonas mobilis*. In another preferred embodiment, the Klebsiella is *Klebsiella oxytoca*.

In a specific embodiment, the recombinant microorganism comprises heterologous nucleic acid molecules encoding *Zymomonas mobilis* pyruvate decarboxylase and alcohol dehydrogenase and *Klebsiella oxytoca* phospho-β-glucosidase and (phosphoenolpyruvate-dependent phosphotransferase system) cellobiose-utilizing Enzyme II. In further specific embodiments, the heterologous nucleic acid molecules are inserted into the microorganism as the single plasmid. In particular embodiments, the heterologous nucleic acid molecules, which are inserted into the microorganism as a single plasmid, are under a common regulatory control which can be either endogenous to or heterologous to the microorganism. In particular embodiments, the heterologous nucleic acid molecules which are inserted into the microorganism as the single plasmid are located on a plasmid in the microorganism. In an alternative embodiment, the heterologous nucleic acid molecules, which are inserted into the microorganism as the single plasmid, are chromosomally integrated in the microorganism as is well known in the art and described in, for example, U.S. Pat. No. 5,424,202 to Ingram et al., U.S. Pat. No. 5,487,989 to Fowler et al. and U.S. Pat. No. 5,554,520 to Fowler et al.

In yet another particular embodiment, the heterologous nucleic acid molecules encoding *Zymomonas mobilis* pyruvate decarboxylase and alcohol dehydrogenase are inserted into the recombinant microorganism in a separate plasmid from the heterologous nucleic acid molecules encoding *Klebsiella oxytoca* phospho-β-glucosidase and (phosphoenolpyruvate-dependent phosphotransferase system) cellobiose-utilizing Enzyme II. In a specific embodiment, at least one of the heterologous nucleic acid molecules inserted in the separate plasmids is under regulatory control which is endogenous to the microorganism. In another specific embodiment, at least one of the heterologous nucleic acid molecules inserted in the separate plasmids is under regulatory control which is heterologous to the microorganism. In further embodiments, at least one of the heterologous nucleic acid molecules inserted in the separate plasmids is located on a plasmid in the microorganism, or alternatively at least one of the heterologous nucleic acid molecules inserted in the separate plasmids is chromosomally integrated in the microorganism.

In yet another aspect, the invention relates to a method for making ethanol comprising the steps of contacting cellobiose with a recombinant microorganism, as described herein. In one embodiment, cellobiose can be contacted with a recombinant microorganism which expresses pyruvate decarboxylase, alcohol dehydrogenase, Klebsiella phospho-β-glucosidase and Klebsiella (phosphoenolpyruvate-dependent phosphotransferase system) cellobiose utilizing Enzyme II. In another embodiment, cellobiose can be contacted with a recombinant microorganism comprising heterologous nucleic acid molecules encoding a Zymomonas pyruvate decarboxylase, a Zymomonas alcohol dehydrogenase, a Klebsiella phospho-β-glucosidase and a Klebsiella (phophoenolpyruvate-dependent phosphotransferase system) cellobiose-utilizing Enzyme II, wherein said molecules are expressed at levels sufficient to convert cellobiose to ethanol. A detailed description of methods suitable for use in this invention can be found in, for example, U.S. Pat. No. 5,028,539 to Ingram et al., U.S. Pat. No. 5,000,000 to Ingram et al., U.S. Pat. No. 5,424,202 to Ingram et al., U.S. Pat. No. 5,487,989 to Fowler et al., U.S. Pat. No. 5,482,846 to Ingram et al., U.S. Pat. No. 5,554,520 to Fowler et al., U.S. Pat. No. 5,514,583 to Picataggio, et al., U.S. Pat. No. 5,821,093 to Ingram et al. and copending applications having U.S.S.N. 08/475,925 filed on Jun. 7, 1995, U.S.S.N. 08/218,914 filed on Mar. 28, 1994, U.S.S.N. 08/833,435 filed on Apr. 7, 1997 and U.S.S.N. 08/834,900, filed on Apr. 7, 1997, the teachings of all of which are hereby incorporated by reference, in their entirety.

EXPERIMENTAL METHODS

Bacterial Strains And Media

*E. coli* KO11 (Ohta, K. et al., *Appl. Environ. Microbiol.* 57:893–900 (1991)) and *K. oxytoca* P2 (Wood, B. E. and L. O. Ingram, *Appl. Environ. Microbiol.* 58:2103–2110 (1992)) were used in all fermentation studies. These strains are derivatives of *E. coli* B and *K. oxytoca* M5A1, respectively, and contain the *Z. mobilis* genes for ethanol production (pdc, adhB) and chloramphenicol acyl transferase (cat). Stock cultures of KO01 and P2 were maintained on modified Luria agar (Atlas, R. M. and L. C. Parks (ed.) *Handbook of Microbiological Media.*, CRC Press, Inc., Boca Raton, Fla. (1993)) containing NaCl (5 g liter$^{-1}$), Yeast Extract (5 g liter$^{-1}$), Tryptone (10 g liter$^{-1}$), glucose (20 g liter$^{-1}$), agar (15 g liter$^{-1}$), and chloramphenicol (0.6 g liter$^{-1}$). Strains KO11 and P2 are prototrophic and recombination proficient. In liquid cultures and fermentation experiments, chloramphenicol was added at a final concentration of 40 mg liter$^{-1}$.

Three plasmids containing genes encoding (phosphoenolpyruvate-dependent phosphotransferase system) cellobiose-utilizing Enzyme II (also referred to as PTS cellobiose uptake) and phospho-β-glucosidase (also referred to as cellobiose cleavage) were used in this study (Lai, et al., *Appl. Environ. Microbiol.* 63:355–363 (1997)): pLOI1903 containing genes from *Bacillus subtilis*, LOI1905 containing genes from *Bacteroides fibrisolvens*, and pLOI1906 containing the *K. oxytoca* cas AB operon. A series of mutant plasmids derived from pLOI1906 were developed and analyzed in this study; pLOI1908, pLOI1909, and pLOI1910.

Utilization of cellobiose (20 g liter$^{-1}$) was screened using MacConkey agar, M9 minimal agar, modified Luria agar containing 4-methylumbelliferyl-glucoside (20 mg liter$^{-1}$) and in Luria broth (Atlas, R. M. and L. C. Parks (ed.) *Handbook of Microbiological Media.*, CRC Press, Inc., Boca Raton, Fla. (1993)) containing cellobiose (60 g liter$^{-1}$). Ampicillin (50 mg liter$^{-1}$) was added for plasmid selection.

In vitro ASSAY OF PTS ACTIVITY

The combined activity of the casAB phosphotransferase system and phospho-cleavage enzyme were determined using p-nitrophenyl-(pNPG) as a substrate essentially as described previously (Lai, X. et al., *Appl. Environ. Microbiol.* 63:355–363 (1997)). Overnight cultures (15 h) were harvested by centrifugation (5,000× g, 5 minute, 4° C.), washed twice, and resuspended in 50 mM NaKHPO$_4$ buffer (pH 7.2) to a density of approximately 50 OD$_{550}$ ml$^{-1}$. Cells were disrupted by two passages through a French pressure cell at 20,000 lb in$^{-2}$. Lysates were assayed at 37° C. in 50 mM NaKHPO$_4$ buffer (pH 7.2) containing 5 mM MgCl$_2$, 2 mM pNPG and 2 mM phosphoenolpyruvate. Reactions were terminated by adding an equal volume of 1 M Na$_2$CO$_3$. After centrifugation (5,000× g, 5 minute) to remove cell debris, p-nitrophenol was measured at 410 nm. Protein was estimated using the Bradford Reagent (Bio-Rad Laboratories, Richmond, Calif.) with bovine serum albumin as a standard. Activities are expressed as $\mu$moles milligram$^{-1}$ cell protein per minute.

Genetic Methods and DNA Sequencing

E. coli DH5α was used as the host for plasmid maintenance. Standard methods were employed for isolation, construction, transformation, and analysis of plasmids (Sambrook et al.) DNA was sequenced by the dideoxynucleotide chain termination method using fluorescent M13 primers (forward, 5'-CACGACGTTGTAAAACGAC-3'(SEQ ID NO:1); reverse, 51-CGATAACAATTTCACACAGG-3' (SEQ ID NO:2)) purchased from LI-COR (Lincoln, Nebr.). A forward custom primer spanning CasA amino acid residues Phe56-Ser50 (AAAGAAGAACAGCGCATCGC) (SEQ ID NO:3) was used to sequence and confirm the 5' junction between *K. oxytoca* and pUC18 by using dNTP and fluorescent-labeled ATP (LI-COR). A reverse custom primer spanning CasB amino acid residues Asn312-Leu318 (AACAAAAAGCGCGCGGCAA) (SEQ ID NO:4) was used to sequence the 3' end of casB and downstream region. Extension reactions were performed as previously described (Lai et al. (1997)) using a Perkin Elmer GeneAmp PCR System 9600 (Norwalk, Conn.) and a SequiTherm Long-Read Cycle Sequencing Kit-LC (Epicentre Technologies, Madison, Wis.). Products were separated and read with a LI-COR DNA Sequencer Model 4000L. Sequences were analyzed using the Wisconsin Genetics Computer Group software package (Devereux, J. et al., *Nucleic Acids Res.* 12:387–395 (1984)).

Batch Fermentations Of Cellobiose

Fermentations (350 ml volume) and analyses were carried out in modified Luria broth essentially as described previously (Beall, D. S. et al., *Biotechnol. Bioeng.* 38:296–303 (1991)) except using cellobiose (90 g liter$^{-1}$) as the fermentable sugar. KOH was automatically added to prevent broth pH from falling below pH 6.0 during fermentation (35° C., 100 rpm). Increases in pH were not controlled. Ethanol was monitored by gas chromatography. Cell mass was measured as optical density at 550 nm. Using Embden-Meyerhof glycolysis and the *Z. mobilis* ethanol pathway, the maximum theoretical yield is 4 moles each of ethanol and CO$_2$ per mole cellobiose (0.538 g ethanol and 0.462 g CO$_2$ per g cellobiose).

Simultaneous Saccharification and Fermentation of Mixed Waste Office Paper

Mixed waste office paper (100 g liter$^{-1}$) was fermented to ethanol essentially as described previously (Brooks et al., *Biotechnology Progress* 11:619–625 (1995))) in 800 ml agitated (60 rpm) vessels (35° C., pH 4.9–5.2). Spezyme CP cellulase was added at a 1:100 dilution and provided approximately 1000 filter paper units liter$^{-1}$ (10 FPU gram$^{-1}$ cellulosic substrate). Fermentations were sampled at 24 hour intervals. No pH control was required after the first 24 hours.

Bacterial Strains, Plasmids, and Growth Conditions

The other bacterial strains and plasmids used in this study are listed in Table 4. *Z. mobilis* strain CP4 was grown in TRG medium at 30° C. Strains of *Escherichia coli* were grown in LB medium at 37° C. (Sambrook). *Klebsiella oxytoca* P2 was grown at 30° C. in LB medium containing 5% sugars. To select recombinant *Z. mobilis* and *E. coli*, 120 or 40 μg/ml chloramphenicol, respectively, were added to the media after sterilization. To test the in vivo activity of cellobiose hydrolysis from recombinant *Z. mobilis*, cellobiose analog, 4-methylumbelliferyl-β-D-glucopyranoside (MUG) (10 μg/ml) (Wood, T., *Methods of Enzymology* 160:87–112 (1988)) was added to solid TRG medium (15 g liter$^{-1}$)

Molecular Biological Techniques

Standard procedures were used for the construction, isolation, analysis, and transformation of recombinant plasmids (Sambrook). PCR was performed with a Perkin-Elmer Gene Amp PCR System 9600 (Perkin Elmer, Norwalk, Conn.). Conjugation of plasmids from *E. coli* to *Z. mobilis* has been described previously (Arfman, *J. Bacteriol.* 174: 7370–7378 (1992)).

In vitro ASSAY FOR THE ACTIVITY OF CELLOBIOSE HYDROLYSIS

Overnight cultures (approximately 20 hours) were harvested by centrifugation (5,000× g, 5 minutes, 4° C.). After washing twice with NaKHPO$_4$ buffer (pH 7.2), cells were resuspended in the same buffer and homogenized by two passes of French pressure cell at 20,000 lb in$^{-2}$. Protein concentration was determined using Bradford Reagent (Bio-Rad Laboratories, Richmond, Calif.) with bovine serum albumin as a standard. The combined activity of PTS phosphotransferase and phospho-cellobiase was measured as described previously (Lai et al., *Appl. Environ. Microbiol.* 63: 355–363(1997). The activity of phospho-cellobiase was measured by using o-nitrophynel β-D-galactopyranoside 6-phosphate (ONPG-P) as a substrate (Fox, PNAS, USA 59: 988-995 (1968)). The reaction was performed in the same buffer containing 5 mM of MgCl$_2$ and 2 mM of ONPG-P. The reaction was terminated by adding equal volume of 1 M Na$_2$CO$_3$. Activity was determined by measuring the amount of o-nitrophenol released.

RESULTS

Isolation of Cellobiose-Positive Mutants of KO11

Previous studies from our laboratory described the cloning of (phosphoenolpyruvate phosphotransferase) cellobiose-utilizing Enzyme II (also referred to as PTS genes for cellobiose uptake) and phospho-β-glucosidase (also referred to as genes for cellobiose cleavage) from seven microorganisms (Lai, X. et al., *Appl. Environ. Microbiol.* 63:355–363 (1997)). Although all were expressed sufficiently in DH5α to allow cleavage of methylumbelliferyl-β-glucopyranoside (MUG), a model substrate, only three DH5α recombinants were positive on cellobiose-MacConkey agar and grew on cellobiose-minimal medium: pLOI1903, pLOI1905, and pLOI1906. When KO11 was transformed with these three plasmids, all recombinants were positive on MUG indicator plates but none were positive on cellobiose-MacConkey agar or cellobiose-minimal medium. Plasmids were reisolated from these KO11 recombinants and transformed back into DH5α. All were positive for cellobiose utilization in DH5α indicating that the presence of functional cas genes. Restriction analysis confirmed that these plasmids appeared unaltered during passage through KO11.

Enrichment cultures of each recombinant were set up at 30° C. using Luria broth containing cellobiose (10 ml broth in 1.8×150 mm culture tubes) to select spontaneous mutants which utilize cellobiose. These were diluted 100-fold every 24 hours over a three week period with continuing incubation of ancestral cultures. Several cultures with KO11 (pLOI1906) became quite dense indicating cellobiose utilization. Clones were isolated from two of these by streaking on cellobiose MacConkey agar. Approximately half of the colonies from each enrichment were raised and dark red, strongly positive for cellobiose utilization. Ten positive clones (strains MM101–MM110) were selected for further testing in unshaken tubes containing Luria broth containing 60 g cellobiose liter$^{-1}$ (Table 2). All grew to 4 times the cell density and produced 4 times as much ethanol as the unmutated KO11 (pLOI1906) or KO11(pUC18). With the mutants, broth pH declined (carbonic acid) to approximately pH 5.6 while that of the parent remained nearer neutrality consistent with the absence of carbohydrate metabolism.

Repeated streaking of the mutant strains on solid medium revealed an instability in six of the ten clones and these clones were discarded. The four stable clones, MM101, MM106, MM108, and MM109 grew well on M9 minimal medium containing cellobiose. FIG. 1 compares the growth of the parental strain and strain MM106 on cellobiose in shaken flasks. As is characteristic for ethanologenic KO11, the growth of MM106 with cellobiose was roughly linear at cell densities about 2 O.D. 550 nm.

TABLE 2

Comparison of Cellobiose-Positive Mutants of KO11 (pLOI1906)

| Strain or mutant | Broth pH (24 h) | Optical Density (550 nm) | Ethanol (g liter$^{-1}$) | Colony Uniformity (solid medium) |
|---|---|---|---|---|
| MM101 | 5.7 | 4.74 | 7.9 | yes |
| MM102 | 5.6 | 4.85 | 7.7 | no |
| MM103 | 5.7 | 5.00 | 8.0 | no |
| MM104 | 5.6 | 4.20 | 7.3 | no |
| MM105 | 5.6 | 4.05 | 7.0 | no |
| MM106 | 5.7 | 4.74 | 7.9 | yes |
| MM107 | 5.7 | 4.80 | 7.7 | no |
| MM108 | 5.6 | 4.42 | 7.4 | yes |
| MM109 | 5.7 | 4.64 | 7.4 | yes |
| MM110 | 5.5 | 4.05 | 6.8 | no |
| KO11 (pUC18) | 6.3 | 1.20 | 1.7 | yes |
| KO11 (pLOI1906) | 6.2 | 1.20 | 1.8 | yes |

Initial Characterization of Cellobiose-Positive Mutants

To investigate the mechanism leading to cellobiose utilization, plasmids were isolated from strains MM101, MM106, MM108, and MM109. After transformation into KO11 and DH5α, all recombinants retained cellobiose utilization ability indicating that plasmid mutations rather than mutation in KO11 were responsible for the acquired phenotype. Restriction analysis revealed that all four plasmids were approximately 500 base pairs smaller than the original pLOI1906. Strains MM106 and MM108 were siblings and only MM106 was retained for study. The plasmids from MM101, MM106, and MM109 were designated as pLOI1908, pLOI1909, and pLOI1910, respectively.

Figure 2A:
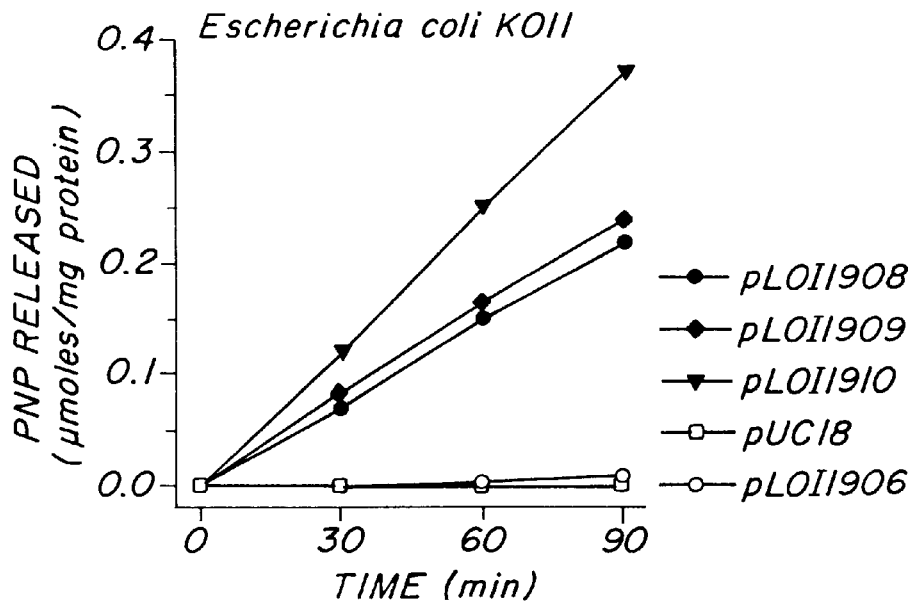
FIG. 2A depicts in vitro comparisons of recombinant strains of *E. coli* KO11 harboring the indicated plasmid, using p-ntirophenyl-β-D-glucoside as a model substrate. Cells were grown in Luria broth containing glucose (50 g liter$^{-1}$).
Figure 2B:
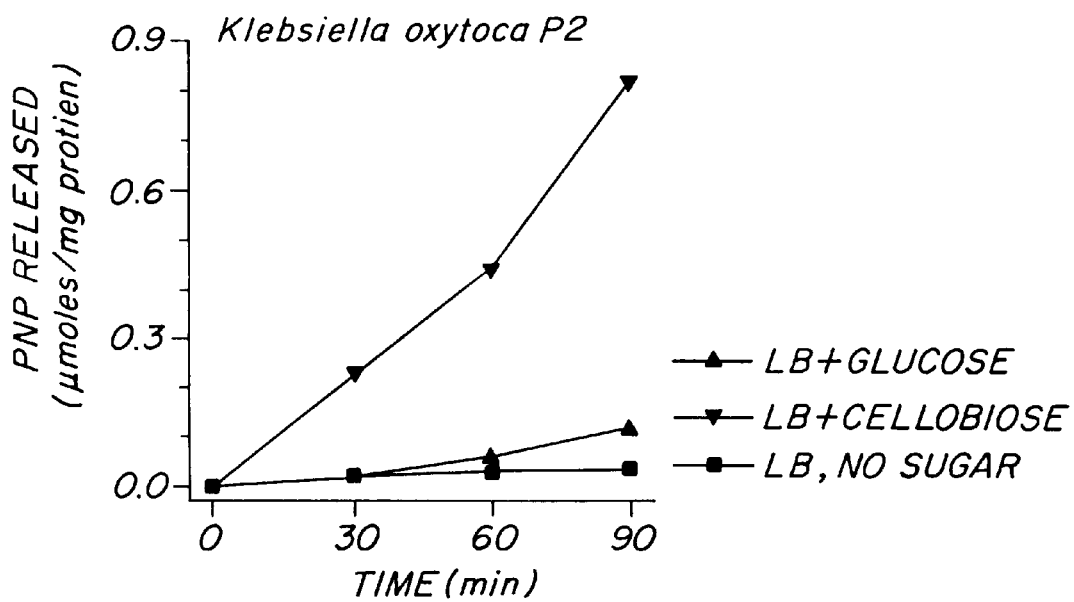
FIG. 2B depicts in vitro comparisons of *K. oxytoca* P2 grown in Luria broth without added sugar, Luria broth containing glucose (50 g liter$^{-1}$), and cellobiose (50 g liter$^{-1}$), using p-nitrophenyl-β-D-glucosied as a model substrate.

Plasmid stocks prepared using DH5α as the host were used to transform native KO11 for further study. The stability of these plasmids in KO11 was examined by serial transfers in the absence of antibiotic selection. After 35 generations, 96% of the colonies which grew on Luria agar with glucose were also positive for cellobiose utilization when tested on cellobiose-MacConkey agar. In vitro expression of the cas operon in KO11 harboring these plasmids was evaluated by measuring the combined PTS transport and cleavage activity using pNPG as a model substrate (FIG. 2A). No activity was present in control strains, KO11 (pUC18) or KO11 harboring the unmutated pLOI1906. The mutant plasmids, pLOI1908, pLOI1909, and pLOI1910 were expressed in KO11 at approximately half the level measured in K. oxytoca P2 grown with cellobiose as an inducer (9 nmoles min$^{-1}$ mg protein$^{-1}$). Interestingly, little activity was detected in K. oxytoca P2 after growth in Luria broth with glucose or in Luria broth without sugar indicating that the native cas operon requires cellobiose for induction (FIG. 2B).

Genetic Analysis of Mutations Facilitating casAB Expression

Figure 3A:
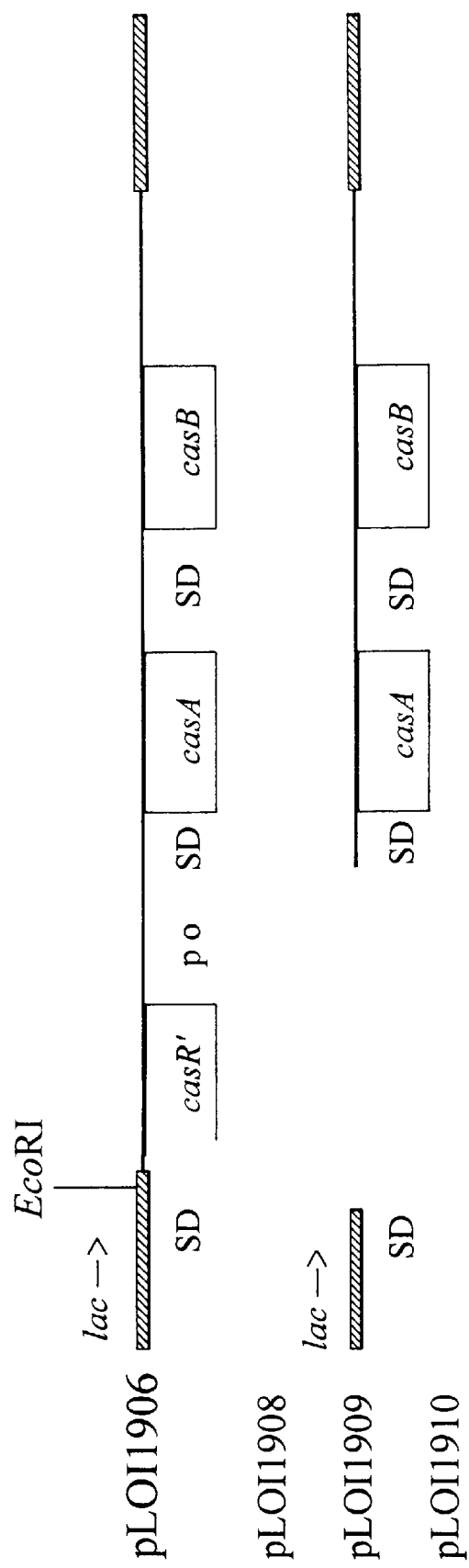
FIG. 3A is a comparison of plasmid pLOI1906 and spontaneous deletions in plasmids pLOI1908, pLOI1909 and pLOI1910 which facilitated expression of the cas operon in *E. coli* KO11. Thick lines represent the vector, pUC 18 thin lines represent DNA derived from *K. oxytoca*.

Mapping with restriction endonuclease enzymes identified a deletion in the 5'-end of the K. oxytoca insert of all three plasmids (loss of the EcoRI site in the vector) while the 3-'end appeared unaltered (FIG. 3A). The lack of deletions at the 3'-end of casB or the junction between the K. oxytoca insert and the vector was confirmed by sequence analysis.

Two patterns of deletion were found in the 5'-end which differed by only two base pairs (FIG. 3B). pLOI1908 and pLOI1909 were shortened by 442 base pairs of K. oxytoca DNA and 37 base pairs of vector DNA in comparison to the original plasmid, pLOI1906. The deletion in pLOI1910 eliminated 441 base pairs of K. oxytoca DNA and 38 base pairs of vector DNA. Thus the results from both recombination events were essentially identical, deleting the incomplete casR; putative casAB promoter and operator regions, and a stem-loop region described Lai et al., (1997). After deletion, the lac Shine-Dalgarno sequence resided only a few base pairs upstream from the casA Shine-Dalgarno region. Expression of casAB in pLOI1908, pLOI1909, and pLOI1910 is dependent upon the lac promoter (vector).

From these results, the expression of casAB from the native promoter (and upstream lac promoter) is more tightly controlled in KO11, a derivative of E. coli B, than in DH5α. The basis of this control may be the palindromic sequence and operator region which are presumed to require binding of an anti-terminator protein+cellobiose for expression in K. oxytoca. The two independent deletions leading to increased expression in KO11 eliminated this regulatory region rather precisely. The resulting plasmids also retained the lac and cas Shine-Dalgarno regions in close proximity which may facilitate increased translation. Recent studies have identified surprising differences in Sigma factors among K12 strains of E. coli (Jishage, M. et al., J. Bacteriol. 179: 959–963). It is possible that variations in Sigma factors or other regulatory proteins may be responsible for the differences in K. oxytoca cas expression between E. coli DH5α and KO11 (E. coli B derivative).

Fermentation of Cellobiose to Ethanol

Figure 4A:
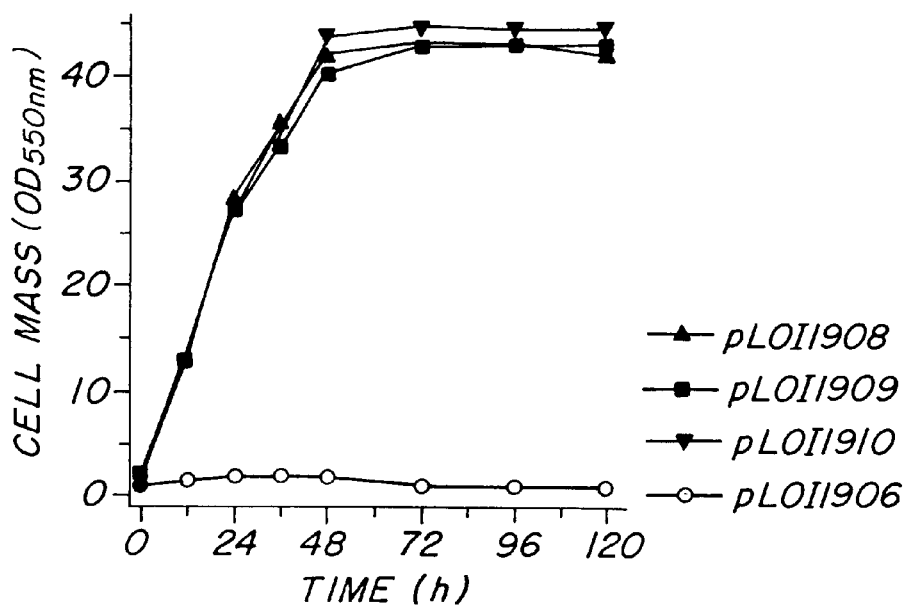
FIG. 4A is a graph depicting ethanol production from fermentation of cellobiose by recombinant strains of *E. coli* having the indicated plsmid.
Figure 4B:
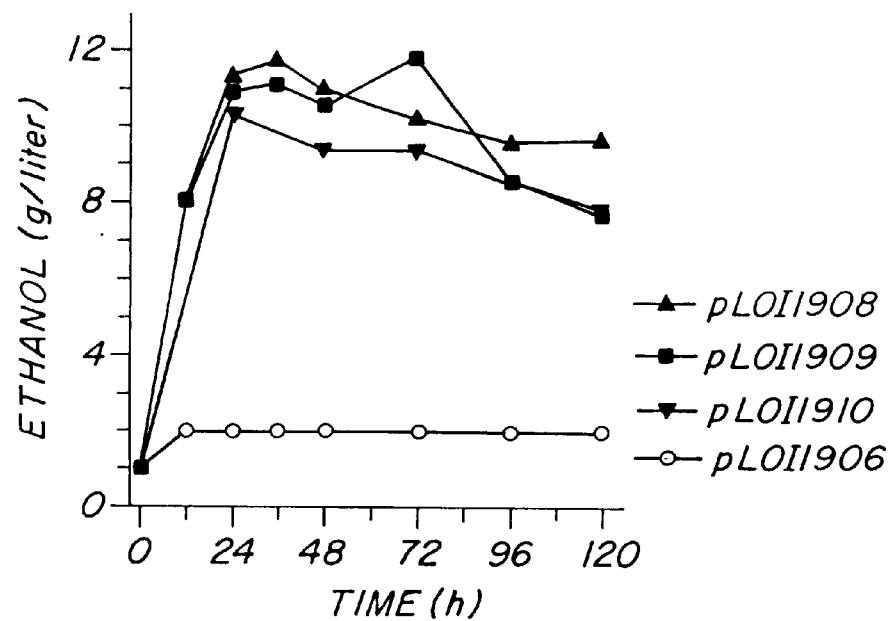
FIG. 4B is a graph representing cell growth from the fermentation of cellobiose by recombinant strains of *E. coli* KO11 having the indicated plasmid.
Figure 5:
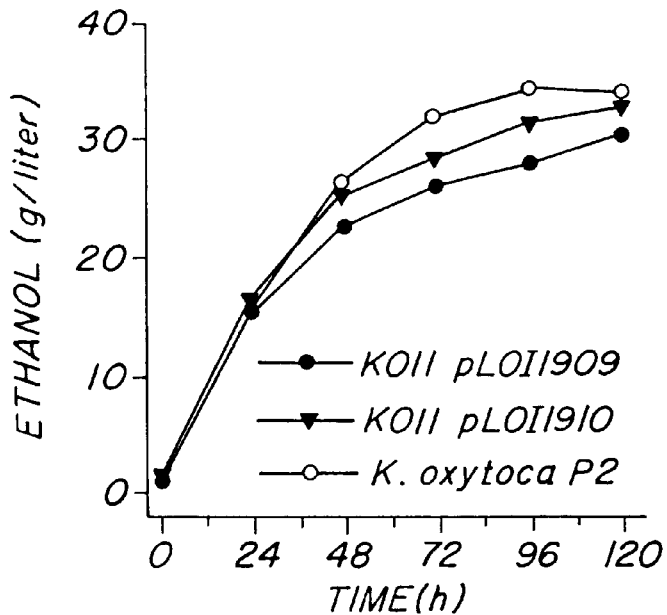
FIG. 5 is a simultaneous saccharification and fermentation of mixed waste office paper (100 g liter$^{-1}$) by *K. oxytaca* P2 and *E. coli* KO11 harboring the indicated plasmids.

Ethanol production from cellobiose was examined using KO11 harboring native pLOI1906 and in vivo deletion mutants (pLOI1908, pLOI1909, and pLOI1910) with increased casAB expression as biocatalysts (FIG. 4). Growth and ethanol production by KO11(pLOI1906) was very poor. KO11 harboring the mutated plasmids produced up to 6-fold higher cell mass, over 20-fold higher ethanol concentrations, and consumed significant amounts of base to maintain pH 6 in comparison to KO11 harboring the original pLOI1906 plasmid (Table 3). Base is typically required by KO11 during sugar fermentation to maintain pH 6 due to the production of large amounts of dissolved $CO_2$ (carbonic acid) and small amounts of acidic fermentation products. Fermentations with the mutants rapidly reached completion and achieved approximately 1 M ethanol. Ethanol yields exceeded 90% of the maximum theoretical yield from cellobiose (0.538 g ethanol gram$^{-1}$ cellobiose)

It is possible to estimate a minimal in vitro rate for cellobiose uptake and hydrolysis by KO11derivatives based on the rate of ethanol production and an estimate of cell mass. Assuming an O.D.$_{550}$ nm of 4.0 represents approximately 1 mg milliter$^{-1}$ of cell protein, the initial rate of cellobiose metabolism is 0.03 μmoles min$^{-1}$ milligram$^{-1}$ protein. This demonstrated in vivo activity is four times higher than the in vitro activity measured in *K. oxytoca* P2 (induced with cellobiose) and ten times higher than the best *E. coli* construct, KO11(pLOI1910) using pNPG as a model substrate.

TABLE 3

Fermentation of cellobiose and mixed waste office paper to ethanol.

| Biocatalyst | Sub-strate (g liter$^{-1}$)[a] | Cell Mass[b] (g liter$^{1}$) | Base Consumed (mmoles liter$^{-1}$) | Ethanol Produced[c] (g liter$^{-1}$) | Yield[d] (% theoretical) |
|---|---|---|---|---|---|
| KO11 (pLOI1908) | cello-biose (90) | 3.9 | 63 | 44.6 | 92 |
| KOII (pLOI1909) | cello-biose (90) | 3.4 | 54 | 44.4 | 92 |
| KO11 (pLOI1910) | cello-biose (90) | 3.1 | 40 | 45.4 | 94 |
| KO11 (pLOI1906) | cello-biose (90) | 0.3 | 0 | 1.0 | 2 |
| KO11 (PLOI1908) | paper (100) | nd | 6 | 30.4 | 67 |
| KO11 (pLOI1910) | paper (100) | nd | 6 | 32.7 | 72 |
| *K. oxytoca* P2[d] | paper (100) | nd | 6 | 34.5 | 76 |

[a]Results represent an average of two or more fermentations. Paper refers to mixed waste office paper.
[b]Cell dry weight.
[c]The theoretical yield is 0.538 g ethanol gram$^{-1}$ cellobiose and 0.568 g ethanol gram$^{-1}$ cellulose. Mixed waste office paper contains approximately 80% cellulose, with a maximum theoretical yield from cellulose of approximately 0.454 g ethanol gram$^{-1}$ mixed office waste paper.
[d]All other biocatalysts are drivatives of *E. coli* B.

TABLE 4

Bacterial strains and plasmids described herein

| Strain/plasmid | Genetic characteristics |
|---|---|
| Strains | |
| *E. coli* | |
| DH5α | FΔlacZM15 recA |
| JLT2 | F recA13 ptsI |
| S17-1 (λpir) | thi pro hsdR recA RP4-TC::Mu-Kn::Tn7 |

TABLE 4-continued

Bacterial strains and plasmids described herein

| Strain/plasmid | Genetic characteristics |
|---|---|
| *K. oxytoca* | |
| P2 | Prototroph |
| *Z. mobilis* | |
| CP4 | Prototroph |
| Plasmids | |
| pUC18 | bla amp lacI'Z' |
| pLOI193 | cat tet |
| pLOI1844 | cat |
| pLOI | pUC 18 containing *B. stearothermophilus* cel |
| pLOI | pUC 18 containing *B. stearothermophilus* ptsHI |
| pLOI1906 | pUC 18 containing *K. oxytoca* casAB |
| pDS20 | pBR22 containing *E. coli* ptsHI |
| pLOI1812 | cel Bs-ptsHI |
| pLOI1832 | lacZ-P pgm-P casAB pgm-T/adhB-P Ec-ptsHI adhB-T |
| pLOI1836 | adhB-P Ec-ptsHI adhB-T |
| pLOI1837 | lacZpP pgm-P casAB pgm-T |
| pLOI1853 | lacZ-P pgm-P casAB/adhB-P Ec-ptsHI |
| pLOI1872 | lacZ-P pgm-P casAB/Ec-ptsHI |
| pLOI1877 | lacZ-P pgm-P casAB/Ec-ptsHI |
| pLOI1882 | adhB-P casAB/Ec-ptsHI |
| pLOI1885 | pgm-P casAB/Ec-ptsHI |
| pLOI1888 | lacZ-P casAB/Ec-ptsHI |

Simultaneous Saccharification and Fermentation of Mixed Waste Office Paper

Previous studies have demonstrated the effectiveness of *K. oxytoca* p2 for the conversion of cellulosic substrates into ethanol (Brooks et al., *Biotechnology Progress* 11: 619–625 (1995)). *E. coli* KO11 derivatives (pLOI1908, pLOI1910) expressing the cas operon from *K. oxytoca* were almost equivalent to P2 for ethanol production from mixed waste office paper (FIG. 4, Table 3). Initial rates of fermentation were similar although P2 achieved a higher final ethanol concentration KO11(pLOI1910), the construct with the highest functional expression of the *K. oxytoca* casAB operon, appeared superior to KO11(pLOI1909) for the conversion of mixed waste office paper to ethanol.

Plasmid Construction

To engineer *Z. mobilis* to use cellobiose, a series of recombinant plasmids were made. All plasmids were constructed on the base of an *E. coli-Z. mobilis* shuttle vector, pLOI193 (Conway, *Appl. Environ. Microbiol.* 53: 235–241 (1987)) and a smaller derivative of modified pLOI193, pLOI1844. pLOI1844 was constructed by deleting a Sfi I/Sac I fragment from pLOI193 and inserting a Sac I linker at this site. After that, a PstI/Cla I fragment was deleted and a Bam HI linker was inserted. The resulting pLOI1844 was deleted entire tetracycline resistant gene and ColEI replicon, and retained all other genes of pLOI193.

All plasmids were constructed by using *E. coli* strain DH5α or JLT2 as hosts. The recombinants with cellobiose genes were recovered by complementing DH5α to use cellobiose, the recombinants with ptsHI operon were isolated by complementing JLT2 to use fructose.

pLOI1812 contained cel (Lai et al., *J. Bacteriol.* 175:6441–6450 (1993) and ptsHI (Lai, Microbology 141:1443–1449, (1995)) operons from *Bacillus stearothermophilus*. It was constructed first by inserting a NotI/SacI fragment of cel operon from pLOI903 (Lai et al., *Appl. Environ. Microbiol.* 63: 355–363 (1997)) into Not I/Sac I sites of pLOI193, then inserting a Not I fragment with ptsHI operon from pLOI800 into the Not I site.

pLOI1836 contained the *E. coli* ptsHI operon which is preceded by *Z. mobilis* adhB promoter and terminated by adhB terminator, its orientation of transcription is opposite to that of a peptide on the vector, pBluescript KSII. The *E. coli* ptsHI operon in this plasmid was isolated from genomic DNA of DH5α by using PCR with two custom primers (5'-ATGTCGACCTATAAGTTGGGGA (SEQ ID NO:5) and 5'-ATGGATCCATGAGAGCGATGAA) (SEQ ID NO:6); this PCR fragment included crr gene and downstream region which might also function as terminator. The *Z. mobilis* adhB promoter was isolated from digestion of pLOI287 (Conway, J. Bacteriol 169: 2591–2597 (1987)); the adhB terminator was isolated from pLOI287 by using PCR with M13 universal forward primer and a custom primer (5'-CCATCGATATCGCCAATCTCGG) (SEQ ID NO:7). To isolate and orientate the adhB promoter opposite to the LacZ promoter, pLOI287 was digested with HincII and EcoRI, the promoter fragment was purified and inserted into HincII/EcoRI sites of pBluescript KSII, then an extra BstEII/SmaI fragment was deleted from this plasmid to form pLOI1861; the PCR fragment of ptsHI operon was first treated with Klenow and inserted into HincII site at pUC18, the crr gene in this plasmid was knocked off by digesting with AccI and Klenow and self ligation to form pLOI1874. To purify ptsHI operon fragment, pLOI1874 was first treated with SacI and Klenow, after denaturing the enzymes, the blunted DNA was digested with HindIII. The purified ptsHI operon was then inserted into pLOI1861 at HincII/HindIII sites to form pLOI1866. The adhB terminator was isolated from pLOI287 by using PCR with one custom primer (5'-CCATCGATATCGCCAATCTCGG) (SEQ ID NO:7) and M13 forward primer. The PCR fragment was first treated with Klenow, then digested with SalI. This digested PCR fragment was then ligated with pBluescript IIKS which was digested with EcoRV and SalI, to form pLOI1838. A DNA fragment containing adhB promoter and ptsHI operon was isolated from pLOI1866 by first digestion with ApaI and Klenow, then SacI. This fragment was inserted into pLOI1838 at SmaI/SacI sites to form pLOI1840. pLOI1840 was then digested with ScaI, shuttle vector, pLOI1844, was digested with BamHI and treated with Klenow. The two digests were then ligated to form pLOI1836.

pLOI1837 contained the *Klebsiella oxytoca* casAB operon; lacZ promoter and *Z. mobilis* pgm promoter were fused with the operon in the upstream and a pgm terminator in the down stream region. The casAB operon and pgm promoter were first combined into pLOI1886. For constructing this plasmid, pLOI1906 was digested with KpnI then treated with Klenow, after denaturing these enzymes, it was digested with HindIII. The fragment with casAB was then purified and inserted into HincII/HindIII sites on pLOI685 (Yomano, *J. Bacteriol.* 175: 3926–3933 (1993)) to form pLOI1886. The pgm terminator was isolated by using PCR with two custom primers (5'-ACGGCCGTTGGTCTACGAATTG (SEQ ID NO:8) and 5'-AAAGCTTCGGCATTGGCTTCGT) (SEQ ID NO:9) and pLOI685 as a template. This PCR fragment was directly inserted into AT vector to form pLOI1839. An EagI/HindIII fragment with pgm promoter was then purified from pLOI1839 and ligated with pLOI1886 which was digested with the same pair of enzymes, to form pLOI1843. pLOI1843 was then digested with ScaI and ligated with shuttle vector pLOI1844 which was digested with BamHI and treated with Klenow to form pLOI1837.

pLOI1888 contained both casAB operon and ptsHI operon. The casAB operon is expressed from lacZ promoter, ptsHI operon is expressed from its native promoter. A plasmid containing *E. coli* ptsHI operon, pDS20 (Saffen, J. Biol. Chem. 262: 16241–16253 (1987)), was digested and treated with BamHI, Klenow, and ClaI in that order after cleaning up the enzymes in each previous step. The DNA fragment containing ptsHI operon was purified and ligated with pLOI193, which had been digested and treated with PstI, Klenow, and ClaI in the order. The resulting plasmid, pLOI1898, was then digested and treated with ClaI and Klenow, and ligated with a BglII/DraI fragment containing casAB operon, which was purified from the digests of pLOI1906, to form pLOI1888.

pLOI1885 contained both casAB operon and ptsHI operon. The casAB had a pgm promoter in front and ptsHI used its native promoter. This plasmid was constructed by fusing DNA fragments from pLOI1898 and pLOI1886. pLOI1886 was digested and treated with SacI, Klenow, and BglII in that order; the DNA fragment containing pgm promoter and casAB operon was then purified and ligated with pLOI8908, which was digested and treated with SfiI, Klenow, and SacI in that order.

pLOI1882 contained both casAB and ptsHI operons. The casAB had an adhB promoter in its front and ptsHI used its native promoter. The casAB operon and adhB promoter were fused to form pLOI1893 by inserting a SacI/HindIII fragment (SacI was blunted by Klenow) of casAB operon from pLOI1906 into pLOI287 on HincII/HindIII sites. A SacI/BglII fragment (BglII was blunted by Klenow) with adhB promoter and casAB operon was then purified and ligated with pLOI1898 at SacI/SfiI sites (SfiI was blunted by Klenow) to form pLOI1882.

pLOI1877 contained both casAB and ptsHI operons. The casAB operon could be expressed from lacZ and pgm promoters. The ptsHI operon was expressed from its native promoter. This plasmid was constructed by fusing DNA fragments from pLOI1898 and pLOI1886. pLOI1898 was served as a vector and contributed ptsHI operon. It was prepared by digesting with SacI, treating with Klenow, then digesting with NotI. The casAB operon with lacZ and pgm promoter in the front was purified from pLOI1886 digests with DraI and EagI. This fragment was then ligated to the prepared pLOI1898. The DraI end was ligated with Klenow treated SacI site on pLOI1898, and EagI end was ligated with NotI on pLOI1898.

pLOI1853 contained both casAB and ptsHI operons. The casAB operon could be expressed from both lacZ and pgm promoters. The ptsHI operon was expressed from adhB promoter. Two operons along with the promoters were first fused in pLOI1879. For constructing this plasmid, pLOI1886 was served as a vector. It was prepared by digestion with XbaI then treated with Klenow. A fragment containing ptsHI operon and adhB promoter was purified from digestion of pLOI1866. One of the ends of this fragment had a Klenow treated ApaI site, another end had a blunt SacII site. The resulting pLOI1879 was then digested with ScaI and ligated to the shuttle vector pLOI1844 which was pre-treated with BamHI and Klenow to form pLOI1853.

pLOI1872 contained both casAB and ptsHI operons. Both operons could be expressed from lacZ and pgm promoters. These DNA were orientated as: lacZ-promoter →pgm-promoter→casAB operon→ptsHI operon. The ptsHI operon was isolated from pDS20 by using PCR with two custom primers (5'-ATGTCGACCTATAAGTTGGGA (SEQ ID NO:10) and 5'-ATGGATCCATGATCTTCTTCTA) (SEQ ID NO:11). This PCR fragment was treated with Klenow then ligated into pUC18 at HincII site to form pLOI1847. A XbaI/HindIII fragment containing the ptsHI operon was then purified from pLOI1847 and ligated to pLOI1886 at XbaI/HindII location to form pLOI1860. pLOI1860 was then digested with ScaI and ligated to shuttle vector pLOI1844 which was pre-treated with BamHI and Klenow to form pLOI1872. pLOI1832 also contained both casAB and ptsHI operons.

The casAB was preceded by lacZ and pgm promoters in the order, and followed by pgm terminator. The ptsHI operon was expressed from adhB promoter and followed by adhB terminator. To construct this plasmid, all the essential DNA fragments from pLOI1843 and pLOI1840 were first combined to form pLOI1833. A HindIII/SacI DNA fragment containing pgm promoter, casAB operon, and pgm terminator was purified from pLOI1843 digestion. After treatment with Klenow, this fragment was ligated into pLOI1840, which was pre-treated with ApaI and Klenow, to form pLOI1833. pLOI1833 was then digested with ScaI and ligated with shuttle vector pLOI1844 which was pretreated with BamHI and Klenow to form pLOI1832.

Expression of PTS and Cellobiase Genes in Z. Mobilis

All the plasmid constructions were conjugated from E. coli strain S17-1 into Z. mobilis CP4 strain. The plasmids were then recovered from recombinant Z. mobilis and transformed back to E. coli to confirm that the plasmids were not mutated. None of the plasmids recovered from Z. mobilis were mutated. After transforming into E. coli JLT2, the recombinant strains could use cellobiose as well as those transformed by the original plasmids, and the pattern of enzyme digestion for these plasmids recovered from recombinant E. coli were the same as those for the original plasmids. The high stability of foreign plasmids in Z. mobilis may reflect its characteristics not as mutable as other common laboratory organisms such as E. coli and Bacillus subtilis.

For the recombinant Z. mobilis strains to metabolize cellobiose or MUG, these substrates were first be phsophorylated and transported into the cells, then cleaved. The Z. mobilis recombinants were tested for this combined activity on the indicator plates of TRG medium containing 10 mg/L MUG. The highest activity was observed from the recombinant Z. mobilis with pLOI1832, which showed bright fluorescent light after overnight incubation on the MUG indicator plate, and the recombinant strain with pLOI1872 showed very weak activity to hydrolyze MUG.

Figure 6:
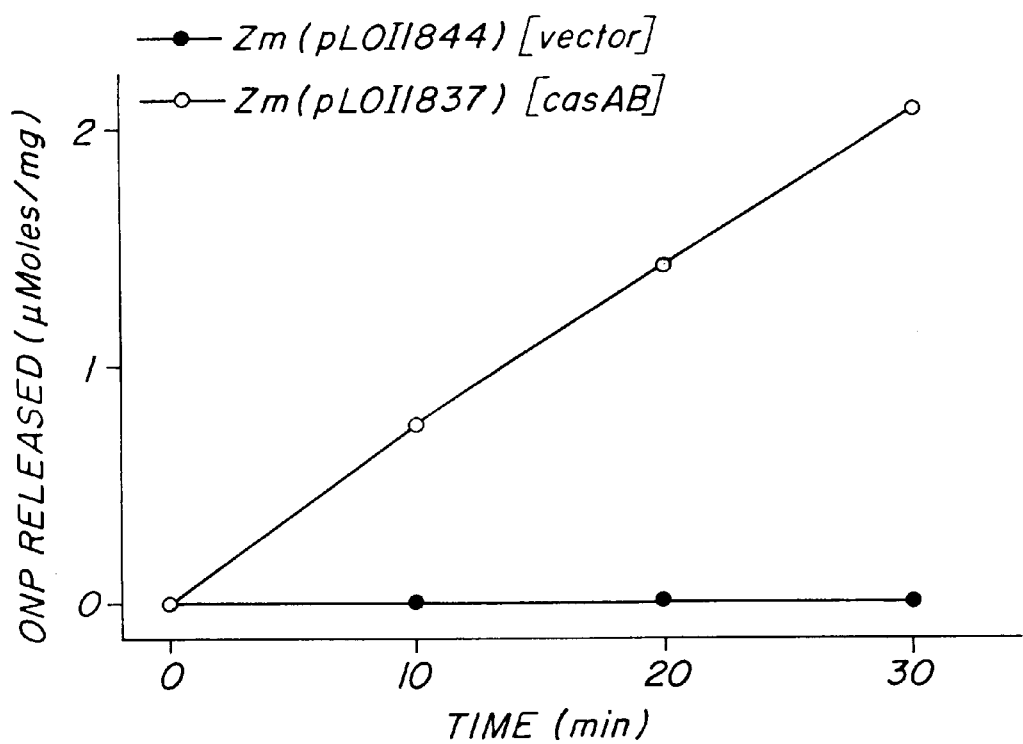
FIG. 6 shows results of an In vitro assay to determine the expression of *K. oxytoca* casAB operon in recombinant *Z. mobilis* with pLOI1837. The activity was measured as the release of o-nitrophenol (ONP) from o-nitrophenyl-6-phosphate (ONPG-P). The result represents an average of three replica.

In vitro assay confirmed that both K. oxytoca casAB and E. coli ptsHI operons could be functionally expressed in Z. mobilis. When assayed with ONPG-P as a substrate significant activity of phospho-cellobiase (casB product) was observed from the recombinant Z. mobilis with pLOI1837 (casAB), while the negative control, recombinant Z. mobilis with the vector pLOI1844, had no activity (FIG. 6).

The in vitro measurement of activity of HPr and enzyme II (ptsHI products) in recombinant Z. mobilis was conducted indirectly by a coupled assay with PNPG as a substrate.

Figure 7:
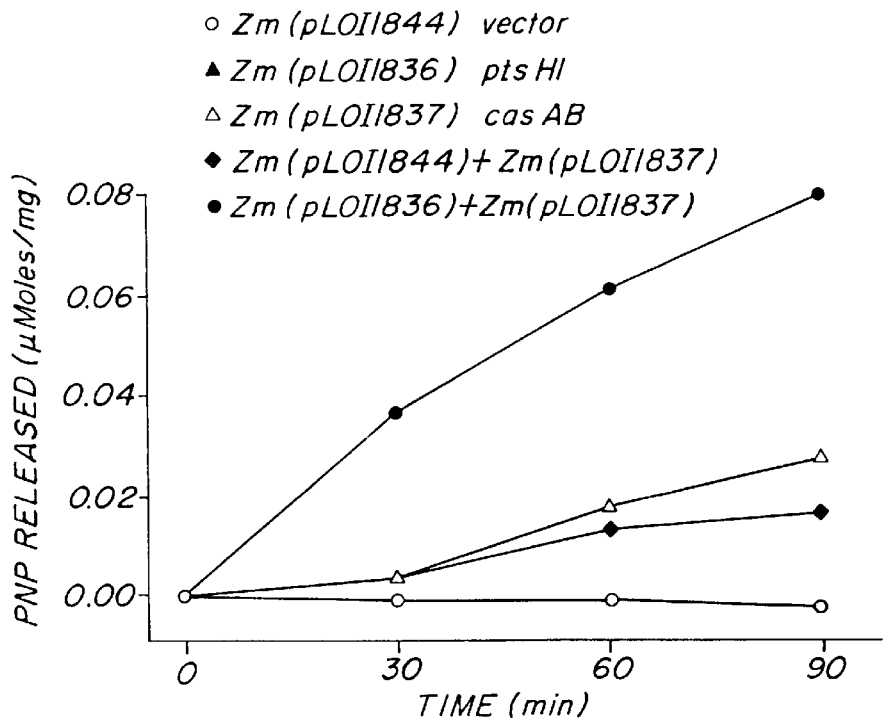
FIG. 7 shows results of an In vitro assay to determine the expression of *E. coli* ptsHI operon in recombinant *Z. mobilis* with pLOI1836. In this coupled assay, PTS enzyme II complex and phospho-cellobiase, expressed from recombinant *Z. mobilis* with pLOI1837, served as couplers. Cell extract from pLOI1837 recombinant [Zm(pLOI1837)] was mixed with that from Zm(pLOI1836). The activity was measured as the release of p-nitrophenol (PNP) from p-nitrophynel-β-D-glucopyranoside (PNPG). The result represents an average of three replica.

The conventional method to measure enzyme I and HPr could not be used for Z. mobilis, since this organism has much higher pyruvate kinase activity than other organisms. The high activity of this enzyme would therefore cover the activities of enzyme I and HPr. The indirect assay uses phospho-cellobiase as a coupler. The phospho-cellobiase, one of the products from pLOI1837, had weak activity on the non-phosphorylated PNPG (FIG. 7). After mixing the cell extracs from pLOI1837 and pLOI1836 recombinants, the PNPG activity increased about three times (FIG. 7). This result indicated that the E. coli ptsHI was functionally expressed in the pLOI1836 recombinant Z. mobilis. These functional HPr and enzyme I, together with enzyme II complex (casA product) expressed in the pLOI1837 recombinant, formed the entire PTS phosphotransferase system. This system was able to phosphorylate PNPG, resulting higher activity from phospho-cellobiase.

Figure 8:
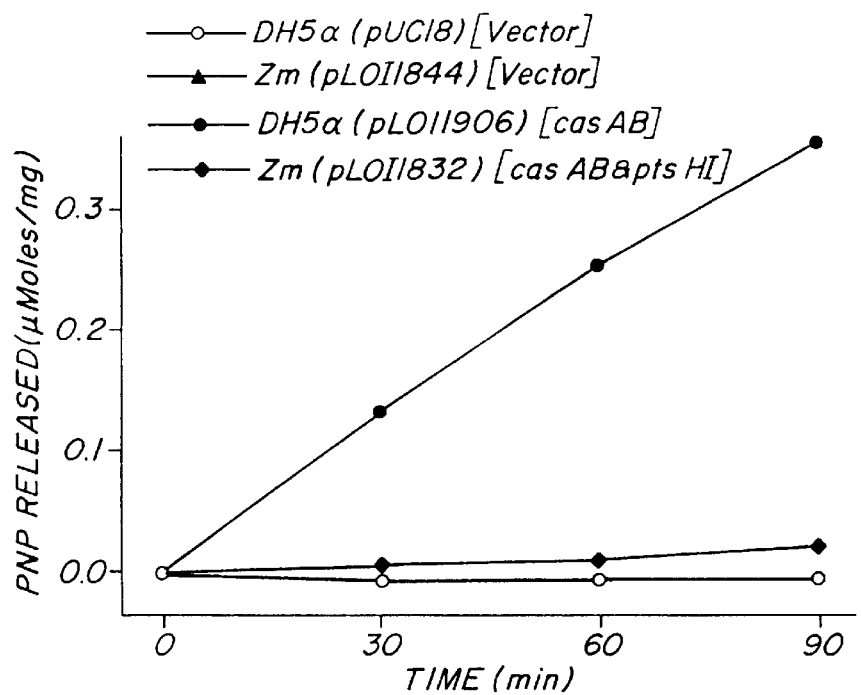
FIG. 8 depicts results of an In vitro comparison of overall activity of cellobiose hydrolysis in recombinant *E. coli* [DH5α(pLOI1906)] and *Z. mobilis* [Zm(pLOI1832)]. The activity was measured as the release of p-nitrophenol (PNP) from p-nitrophynel-β-D-glucopyranoside (PNPG). The result represents an average of three replica.
Figure 9:
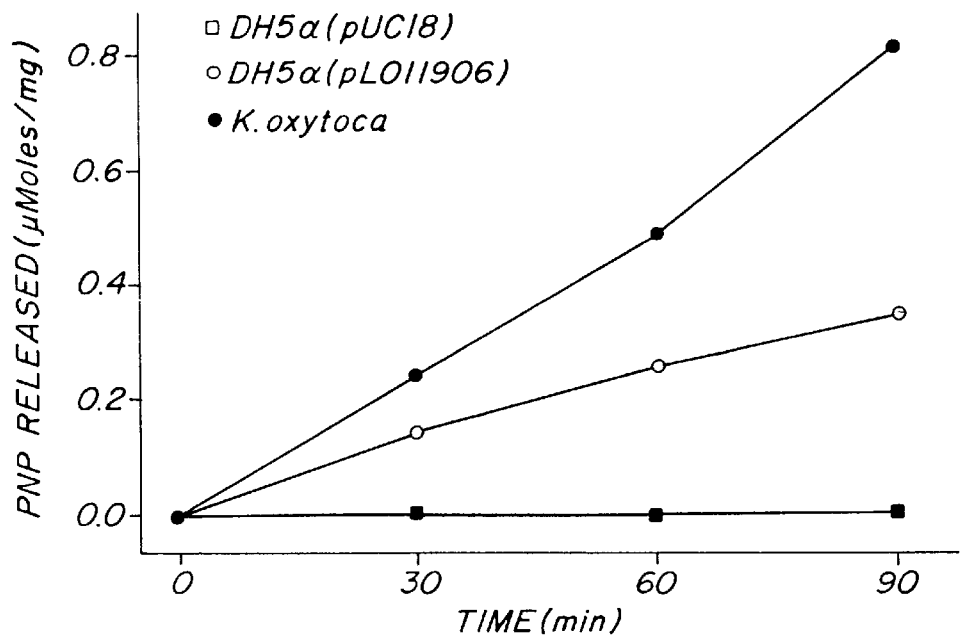
FIG. 9 shows results of an In vitro comparison of overall activity of cellobiose hydrolysis in *K. oxytoca* and recombinant *E. coli*. The activity was measured as the release of p-nitrophenol (PNP) from p-nitrophynel-β-D-glucopyranoside (PNPG). The result represents an average of three replica.

When comparing the overall activities of cellobiose hydrolysis from recombinant E. coli with pLOI1906 and recombinant Z. mobilis with pLOI1832 with PNPG as assay substrate, the activity from the recombinant E. coli was about 15 times higher than that from the recombinant Z. mobilis (FIG. 8). However, this overall activity of DH5α9pLOI1906) was only less than half of that from K. oxytoca P2 strain (FIG. 9).

Figure 10:
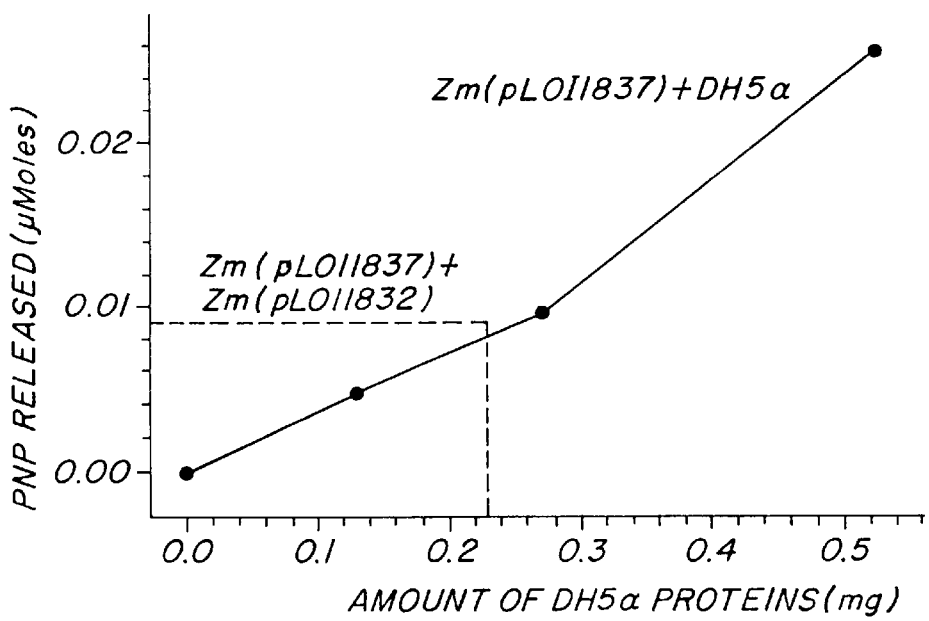
FIG. 10 depicts estimation of the expression of *E. coli* ptsHI operon in *Z. mobilis* using *E. coli* (DH5α) as a standard. In this coupled assay, PTS enzyme II complex and phospho-cellobiase, expressed from recombinant Z. mobilis with pLOI1837, were served as couplers. The activity was measured as the release of p-nitrophenol (PNP) from p-nitrophynel-β-D-glucopyranoside (PNPG). The dash lines represent the activity from Zm(pLOI1832) and corresponding amount of DH5α cell extract. The result represents an average of three replica.
Figure 11:
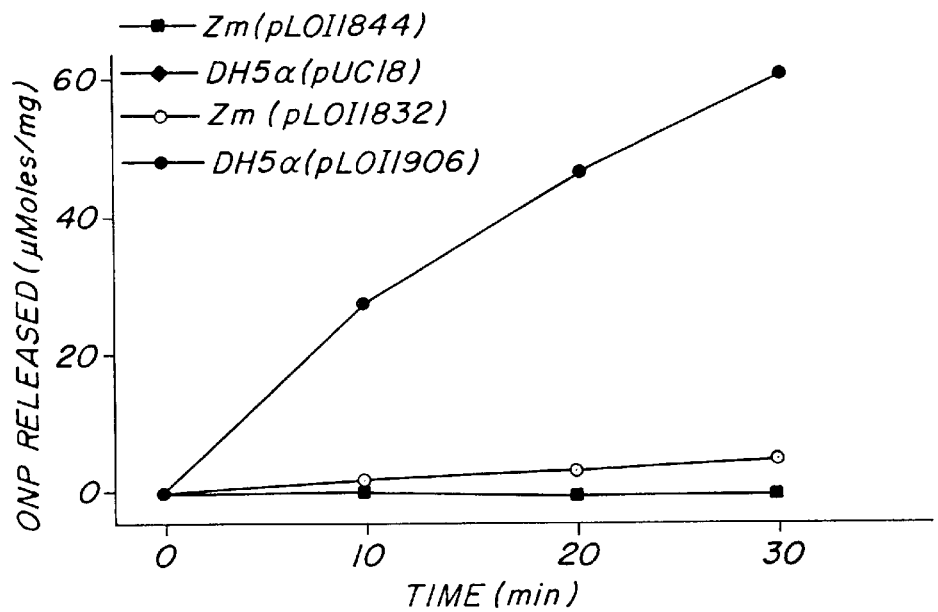
FIG. 11 depicts estimation of the expression of K. oxytoca casB operon in Z. mobilis using recombinant E. coli DH5α (pLOI1906) as a standard. The activity was measured as the release of o-nitrophenol (ONP) from o-nitrophenyl-β-D-galactopyranoside 6-phosphate (ONPG-P). The result represents an average of three replica.

To investigate the rate limiting step of cellobiose hydrolysis in the recombinant Z. mobilis, the relative activities of enzyme I and HPr as well as phospho-cellobiase were estimated to compare those from E. coli DH5α and DH5α (pLOI1906), which could grow on cellobiose minimal medium. The results for the enzyme I and HPr estimation were shown in FIG. 10. In this coupled assay, recombinant Z. mobilis with pLOI1837 provided with enzyme II complex and phospho-cellobiase, and its amount kept to excess and constantly. The reaction was performed for 30 minutes. As the amount of DH5α cell extract increased, the PNP released from PNPG increased. When 0.23 mg cell extract of recombinant Z. mobilis with pLOI1832 was used to instead DH5α, about 0.009 μmoles PNP was released, which amount corresponded to that released from 0.59 mg DH5α cell extract. Therefore, the enzyme I and HPr expressed in the recombinant Z. mobilis was more than one third of those in DH5α (0.23/0.59=39%). The estimation of activity of phospho=-cellobiase is shown in FIG. 11. This activity from Z. mobilis was only less than one tenth of that from DH5α(pLOI1906), however, was comparable with that from K. oxytoca.

The fully functional system for cellobiose hydrolysis includes active PTS enzyme I, HPr, enzyme II complex, and phospho-cellobiase. The results from above in vitro assay indicates that low overall activity of cellobiose hydrolysis in recombinant Z. mobilis might result from low activity of the enzyme II complex (casA product), since part of this enzyme (EIIC domain) must be integrated into the membrane in order to fold properly and to function actively. Although the phospho=-cellobiase activity from recombinant E. coli is much higher than that from K. oxytoca (FIG. 11), the overall activity is only less than half of that from K. oxytoca, indicating the K. oxytoca enzyme II complex might not be properly folded in the E. coli membrane so that it might not be as active as in the native K. oxytoca cells. The same problem could happen in Z. mobilis. Another possible reason for low overall activity might be the complementation of E. coli enzyme I and HPr with K. oxytoca cellobiose specific enzyme II complex, which would result in poor phosphorylation of cellobiose and poor transport.

Expression of heterologous genes in microbial expression systems depends on components of the system. One of the most important components is the promoter. The major difference between plasmid pLOI1977 and pLOI1872 was the promoters for the ptsHI operon. In pLOI1877, ptsHI operon was expressed from its native E. coli promoter. In pLOI1972, lacZ and pgm promoters were responsible for the expression of ptsHI operon. The casAB operon on both plasmids were expressed from lacZ and pgm promoters. Both plasmids recovered ptsI function of a ptsI mutant E. coli strain, JLT2, and permitted this mutant to grow on cellobiose minimal medium. However, the recombinant Z. mobilis with pLOI1872 had weak activity to hydrolyze MUG, while that with pLOI1877 had no activity. These results indicated that the native promoter of E. coli ptsHI might not function in Z. mobilis.

Terminator is another important component in the expression. Other have reported that stem-loop at the 3' end of gap-pgk operon of Z. mobilis is a transcriptional terminator both in *Z. mobilis* and *E. coli*, required to stabilize the full-length gap-pgk message. The 3' stem-loops have also been reported as required to block degradation by abundant 3' to 5' exoribonucleases in *E. coli* and other bacteria. In this study, the presence of stem-loops helped the expression greatly. The recombinant *Z. mobilis* with pLOI1853, which did not include stem-loops for the operons, did not show any activity on the indicator plates, while that with pLOI1832, which included respective stem-loops for the operons, showed high activity to hydrolyze MUG on the indicator plates. These stem-loops might function as transcriptional terminators to stabilize the messages of casAB and ptsHI operons in *Z. mobilis*. But these stem-loops may not be necessary in *E. coli*, since recombinant *E. coli* strains with these two plasmids displayed the characteristics of the two operons equally well. The higher rate of transcription in *E. coli* might compensate the degradation of messages by the exoribonucleases.

Figure 12:
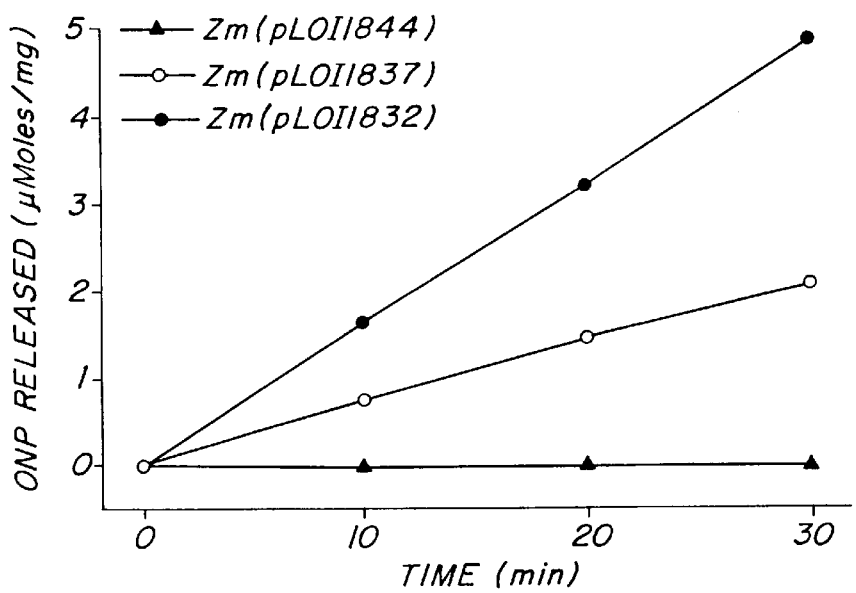
FIG. 12 shows results of an In vitro assay to determine the effect of expression of ptsHI operon on the expression of casAB operon in Z. mobilis. The activity was measured as the release of o-nitrophenol (ONP) from o-nitrophenyl-β-D-galactopyranoside 6-phosphate (ONPG-P). The result represents an average of three replica.
Figure 13:
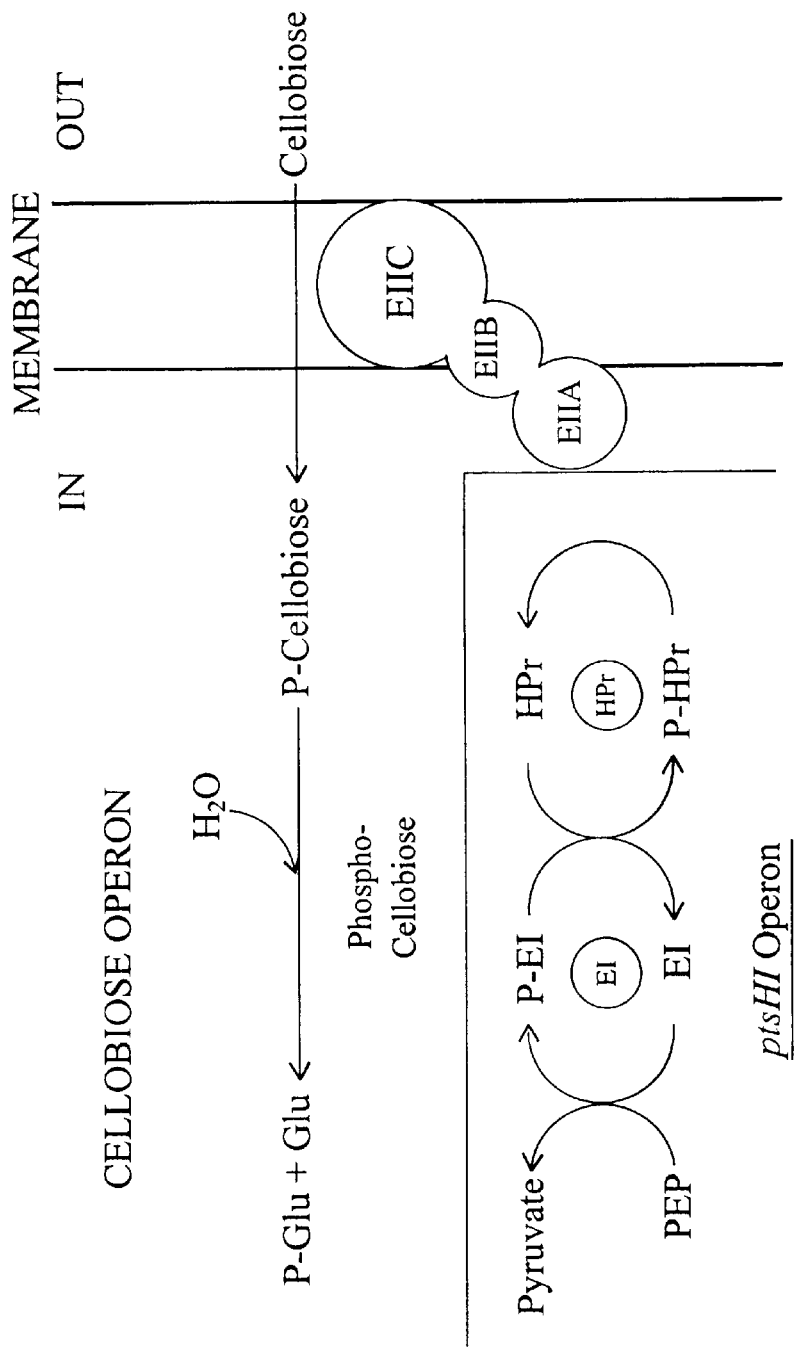
FIG. 13 shows a model for cellobiose metabolism in certain bacteria.

The expression of ptsHI operon appeared to help the expression of casAB operon in *Z. mobilis* (FIG. 12). The difference between pLOI1832 and pLOI1837 was that pLOI1832 included both expressible casAB and ptsHI operons (FIG. 10 and FIG. 11), while pLOI1837 contained expressible casAB operon only (FIG. 6). Other components on these two plasmids were the same, including same vector, location on the vector, as well as promoter and terminator for the casAB operon. However, the activity of phospho-cellobiase (casB product) from *Z. mobilis* recombinant with pLOI1832 was more than double than that in the recombinant with pLOI1837.

SUMMARY OF RESULTS

In engineered *Z. mobilis* strain CP4(pLOI1832), casAB and ptsHI are functionally expressed as demonstrated by the use of chromogenic cellobiose analogues. 4-Methyl-umbelliferyl-β-D-glucopyranoside is transported into cell, phosphorylated, and cleaved into a chromogenic (fluorescent) product (4-methylumbelliferone) and glucose-phosphate which is readily observed on indicator plates in vitro, p-nitrophenyl-β-D-glucopyranoside is phosphorylated and cleaveD into a chromogenic product (p-nitrophenol) and glucose-phosphate. Constructs lacking either the ptsHI operon or casAB operon do not exhibit these activities, but can be mixed in vitro and the activity reconstituted.

However, the overall activity of the uptake process in the best recombinant *Z. mobilis*, CP4(pLOI1832) still does not metabolize cellobiose fast enough to support growth on this substrate in the absence of another fermentable sugar.

Activities of InzI and Hpr are estimated to be approximately ⅓ of that present in *E. coli*, an organism which effectively uses these general proteins for the transport and phosphorylation of many sugars via PTS enzymes. The casB product, the phospho-β-glucosidase, is expressed at a level equivalent to *K. oxytoca*, an organism which is very proficient in the fermentation of cellobiose. Table 5 summarizes the in vivo activity of cellobiose hydrolysis of recombinant *Zymomonas mobilis*, of the invention.

TABLE 5

In vivo Activity of Cellobiose Hydrolysis of Recombinant *zymomonas mobilis*

| Plasmid Number | Genes/Promoters (P)/Terminators (T) | MUG Activity in. *Z. mobilis* |
|---|---|---|
| pLOI1844 | Vector | – |
| pLOI1810 | Bs-cel | – |
| pLOI1812 | Bs-cel/Bs-ptsHI | – |
| pLOI1836 | Zm-adhB-P→Ec-ptsHI→Zm-adhB-T | – |
| pLOI1894 | lacZ-P→Ko-casAB | – |
| pLOI1852 | lacZ-P→Zm-pgm-P→Ko-casAB | – |
| pLOI1837 | lacZ-P→Zm-pgm-P→Ko-casAB→Zm-pgm-T | – |
| pLOI1888 | lacZ-P→Ko-casAB/Ec-ptsHI | – |
| pLOI1885 | Zm-pgm-P→Ko-casAB/Ec-ptsHI | – |
| pLOI1882 | Zm-adhB-P→Ko-casAB/Ec-ptsHI | – |
| pLOI1877 | lacZ-P→Zm-pgm-P→Ko-casAB/Ec-ptsHI | – |
| pLOI1853 | lacZ-P→Zm-pgm-P→Ko-casAB/ Zm-adhB-P→Ec-ptsHI | – |
| pLOI1872 | lacZ-P→Zm-pgm-P→Ko-casAB→Ec-ptsHI | + |
| pLOI1832 | lacZ-P→Zm-pgm-P→Ko-casAB→Zm-pgm-T/ Zm-adhB-P→Ec-ptsHI→Zm-adhB-T | +++ |

EQUIVALENTS

Those skilled in the art will know, or be able to ascertain, using no more than routine experimentation, many equivalents to the specific embodiments of the invention described herein. These and all other equivalents are intended to be encompassed by the following claims.

We claim:

1. A recombinant microorganism which expresses pyruvate decarboxylase, alcohol dehydrogenase, phospho-β-glucosidase and (phosphoenolpyruvate-dependent phosphotransferase system) cellobiose-utilizing Enzyme II, wherein said phospho-β-glucosidase and said (phosphoenolpyruvate-dependent phosphotransferase system) cellobiose-utilizing Enzyme II are heterologous to said microorganism, and said phospho-β-glucosidase has the same amino acid sequence as or has an amino acid sequence with at least about 95% sequence homology in an amino acid alignment to *Klebsiella oxytoca* phospho-β-glucosidase, and said (phosphoenolpyruvate-dependent phosphotransferase system) cellobiose-utilizing Enzyme II has the same amino acid sequence as or has an amino acid sequence with at least about 95% sequence homology in an amino acid alignment to *Klebsiella oxytoca* (phosphoenolpyruvate-dependent phosphotransferase system) cellobiose-utilizing Enzyme II.

2. The recombinant microorganism according to claim 1 wherein said pyruvate decarboxylase and alcohol dehydrogenase are heterologous to said microorganism.

3. The recombinant microorganism according to claim 1 wherein said pyruvate decarboxylase is encoded by a nucleic acid molecule of Zymomonas origin.

4. The recombinant microorganism according to claim 1 wherein said alcohol dehydrogenase is encoded by a nucleic acid molecule of Zymomonas origin.

5. The recombinant microorganism according to claim 1 wherein said pyruvate decarboxylase has the same amino acid sequence as or has an amino acid sequence with at least about 95% sequence homology in an amino acid alignment to *Zymomonas mobilis* pyruvate decarboxylase.

6. The recombinant microorganism according to claim 1 wherein said alcohol dehydrogenase has the same amino acid sequence as or has an amino acid sequence with at least about 95% sequence homology in an amino acid alignment to *Zymomonas mobilis* alcohol dehydrogenase.

7. The recombinant microorganism according to claim 1 wherein said phospho-β-glucosidase is encoded by a nucleic acid molecule of *Klebsiella oxytoca* origin.

8. The recombinant microorganism according to claim 1 wherein said (phosphoenolpyruvate-dependent phosphotransferase system) cellobiose-utilizing Enzyme II is encoded by a nucleic acid molecule of *Klebsiella oxytoca* origin.

9. A recombinant microorganism comprising heterologous nucleic acid molecules encoding a Zymomonas pyruvate decarboxylase, a Zymomonas alcohol dehydrogenase, a Klebsiella phospho-β-glucosidase and a Klebsiella (phosphoenolpyruvate-dependent phosphotransferase system) cellobiose-utilizing Enzyme II, wherein said molecules are expressed at levels sufficient to convert cellobiose to ethanol, and said nucleic acid molecules are heterologous to said microorganism.

10. The recombinant microorganism according to claim 9 wherein said Zymomonas is *Zymomonas mobilis*.

11. The recombinant microorganism according to claim 10 wherein said Klebsiella is *Klebsiella oxytoca*.

12. A recombinant microorganism comprising nucleic acid molecules that encode a *Zymomonas mobilis* pyruvate decarboxylase, a *Zymomonas mobilis* alcohol dehydrogenase, a *Klebsiella oxytoca* phospho-β-glucosidase., and a *Klebsiella oxytoca* (phosphoenolpyruvate-dependent phosphotransferase system) cellobiose-utilizing Enzyme II, wherein said nucleic acid molecules are heterologous to said microorganism.

13. The recombinant microorganism according to claim 12 wherein said heterologous nucleic acid molecules are inserted into said microorganism as a single plasmid.

14. The recombinant microorganism according to claim 13 wherein said heterologous nucleic acid molecules are under a common regulatory control.

15. The recombinant microorganism according to claim 14 wherein said regulatory control is endogenous to the microorganism.

16. The recombinant microorganism according to claim 14 wherein said regulatory control is heterologous to the microorganism.

17. The recombinant microorganism according to claim 14 wherein said heterologous nucleic acid molecules are located on a plasmid in the microorganism.

18. The recombinant microorganism according to claim 13 wherein said heterologous nucleic acid molecules are chromosomally integrated in the microorganism.

19. The recombinant microorganism according to claim 12 wherein said heterologous nucleic acid molecules obtained from *Zymomonas mobilis* are inserted into said microorganism in a separate plasmid from said heterologous nucleic acid molecules obtained from *Klebsiella oxytoca*.

20. The recombinant microorganism according to claim 19 wherein at least one of said heterologous nucleic acid molecules is under regulatory control which is endogenous to the microorganism.

21. The recombinant microorganism according to claim 19 wherein at least one of said heterologous nucleic acid molecules is under regulatory control which is heterologous to the microorganism.

22. The recombinant microorganism according to claim 19 wherein at least one of said heterologous-nucleic acid molecules is located on a plasmid in the microorganism.

23. The recombinant microorganism according to claim 19 wherein at least one of said heterologous nucleic acid molecules is chromosomally integrated in the microorganism.

24. The recombinant microorganism according to claim 9 wherein said microorganism has been further mutated and said molecules are expressed at levels sufficient to convert cellobiose to ethanol.

25. The recombinant microorganism of claim 24 wherein said microorganism has been subjected to an enrichment selection.

26. The recombinant microorganism of claim 24 wherein said microorganism has been contacted with a mutagen.

27. A recombinant nucleic acid molecule comprising nucleic acid molecules encoding pyruvate decarboxylase, alcohol dehydrogenase, Klebsiella phospho-β-glucosidase and Klebsiella (phosphoenolpyruvate-dependent phosphotransferase system) cellobiose-utilizing Enzyme II.

28. The recombinant nucleic acid molecule according to claim 27 wherein said pyruvate decarboxylase and alcohol dehydrogenase are of Zymomonas origin.

29. A method for making ethanol comprising the steps of contacting cellobiose with a recombinant microorganism according to claim 1.

30. A method for making ethanol comprising the steps of contacting cellobiose with a recombinant microorganism according to claim 9.

31. A recombinant microorganism which expresses pyruvate decarboxylase, alcohol dehydrogenase, Klebsiella phospho-β-glucosidase and Klebsiella (phosphoenolpyruvate-dependent phosphotransferase system) cellobiose-utilizing Enzyme II, wherein said phospho-β-glucosidase and said (phosphoenolpyruvate-dependent phosphotransferase system) cellobiose-utilizing Enzyme II are heterologous to said microorgansim.

32. The recombinant microorganism according to claim 31 wherein said pyruvate decarboxylase and alcohol dehydrogenase are heterologous to said microorganism.

33. The recombinant microorganism according to claim 31 wherein said pyruvate decarboxylase is encoded by a nucleic acid molecule of Zymomonas origin.

34. The recombinant microorganism according to claim 31 wherein said alcohol dehydrogenase is encoded by a nucleic acid molecule of Zymomonas origin.

35. The recombinant microorganism according to claim 31 wherein said pyruvate decarboxylase has the same amino acid sequence or has an amino acid sequence with at least about 95% sequence homology in an amino acid alignment to *Zymomonas mobilis* pyruvate decarboxylase.

36. The recombinant microorganism according to claim 31 wherein said alcohol dehydrogenase has the same amino acid sequence or has an amino acid sequence with at least about 95% sequence homology in an amino acid alignment to *Zymomonas mobilis* alcohol dehydrogenase.

37. The recombinant microorganism according to claim 31 wherein said phospho-β-glucosidase is encoded by a nucleic acid molecule of *Klebsiella oxytoca* origin.

38. The recombinant microorganism according to claim 31 wherein said (phosphoenolpyruvate-dependent phosphotransferase system) cellobiose-utilizing Enzyme II is encoded by a nucleic acid molecule of *Klebsiella oxytoca* origin.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CACGACGTTG TAAAACGAC                                   19

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CGATAACAAT TTCACACAGG    20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

AAAGAAGAAC AGCGCATCGC    20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AACAAAAAAG CGCGCGGCAA    20

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

ATGTCGACCT ATAAGTTGGG GA    22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

ATGGATCCAT GAGAGCGATG AA    22

(2) INFORMATION FOR SEQ ID NO:7:

(i) SEQUENCE CHARACTERISTICS:

```
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CCATCGATAT CGCCAATCTC GG                                             22

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ACGGCCGTTG GTCTACGAAT TG                                             22

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AAAGCTTCGG CATTGGCTTC GT                                             22

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ATGTCGACCT ATAAGTTGGG A                                              21

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ATGGATCCAT GATCTTCTTC TA                                             22
```